United States Patent
Grönberg

(10) Patent No.: US 10,451,626 B2
(45) Date of Patent: Oct. 22, 2019

(54) METHOD FOR DETECTING A SOLID TUMOR CANCER

(71) Applicant: PHADIA AB, Uppsala (SE)

(72) Inventor: Henrik Grönberg, Stockholm (SE)

(73) Assignee: PHADIA AB, Uppsala (SE)

(*) Notice: Subject to any disclaimer, the term of this patent is extended or adjusted under 35 U.S.C. 154(b) by 141 days.

(21) Appl. No.: 15/124,769

(22) PCT Filed: Mar. 11, 2015

(86) PCT No.: PCT/SE2015/050272
§ 371 (c)(1),
(2) Date: Sep. 9, 2016

(87) PCT Pub. No.: WO2015/137870
PCT Pub. Date: Sep. 17, 2015

(65) Prior Publication Data
US 2017/0108501 A1    Apr. 20, 2017

(30) Foreign Application Priority Data

Mar. 11, 2014 (SE) .................... 1450274
Apr. 4, 2014 (SE) .................... 1450420

(51) Int. Cl.
*G01N 33/574* (2006.01)
*C12Q 1/6886* (2018.01)
*G06F 19/00* (2018.01)

(52) U.S. Cl.
CPC ..... *G01N 33/57434* (2013.01); *C12Q 1/6886* (2013.01); *G01N 33/57473* (2013.01); *G01N 33/57484* (2013.01); *G06F 19/34* (2013.01); *C12Q 2600/156* (2013.01); *G01N 2333/52* (2013.01); *G01N 2333/96455* (2013.01)

(58) Field of Classification Search
CPC .............................. G01N 33/57434
USPC ............................................ 702/19
See application file for complete search history.

(56) References Cited

U.S. PATENT DOCUMENTS

| | | |
|---|---|---|
| 2011/0301863 A1 | 12/2011 | Auribault et al. |
| 2012/0021925 A1 | 1/2012 | Atnikov et al. |
| 2012/0150032 A1 | 6/2012 | Gudmundsson et al. |
| 2012/0202888 A1 | 8/2012 | Ma |
| 2013/0178393 A1 | 7/2013 | Doll et al. |
| 2013/0196868 A1 | 8/2013 | Lebowitz et al. |

FOREIGN PATENT DOCUMENTS

| | | |
|---|---|---|
| JP | 2013-531997 A | 8/2013 |
| KR | 20080025489 A | 3/2008 |
| WO | 03/100079 A1 | 12/2003 |
| WO | 2006/113210 A2 | 10/2006 |
| WO | 2010/012823 A1 | 2/2010 |
| WO | 2010/081240 A1 | 7/2010 |
| WO | 2010/093939 A2 | 8/2010 |
| WO | 2012/031207 A2 | 3/2012 |
| WO | 2012/092336 A2 | 7/2012 |
| WO | 2013/172779 A2 | 11/2013 |

OTHER PUBLICATIONS

Vickers et al., (Eur Urol. Nov. 2009;56(5):753-760). (Year: 2009).*
Official Action from European Application No. 13792689.5, dated Aug. 1, 2016.
Official Action from European Application No. 13792689.5, dated Mar. 21, 2016.
Official Action from Chinese Application No. 201380069472.6, dated May 9, 2016, and English Translation.
Search Report from Chinese Application No. 201380069472.6, dated May 9, 2016, and English Translation.
Aly et al., Polygenic Risk Score Improves Prostate Cancer Risk Prediction: Results from the Stockholm-1 Cohort Study, European Urology, 60:21-28 (2011).
Nichol MB et al., Cost-effectiveness of Prostate Health Index for Prostate Cancer Detection, BJU Int., 110:353-362 (Nov. 11, 2011).
Brown et al., Macrophage Inhibitory Cytokine1: A New Prognostic Marker in Prostate Cancer, Clin Cancer Res, 15(21):of 1-7 (2009).
Thomsen et al., Prostate-specific antigen doubling time as a progression criterion in an active surveillance programme for patients with localised prostate cancer, BJU Int., 113:E98-E105 (Jul. 19, 2013).
Shiiki et al., Association between saliva PSA and serum PSA in conditions with prostate adenocarcinoma, Biomarkers, 16(6):498-503 (2011).

(Continued)

*Primary Examiner* — Jerry Lin
(74) *Attorney, Agent, or Firm* — Porter Wright Morris & Arthur LLP

(57) ABSTRACT

A method for indicating a presence or non-presence of a predefined solid tumor cancer in an individual, comprising the steps of: A. Providing at least one biological sample originating from said individual at a first point in time; B. Providing at least one biological sample originating from said individual at a second point in time; C. In said at least two biological samples, measuring a presence or concentration of at least one biomarker related to said predefined solid tumor cancer; D. Combining data regarding the presence or concentration of the at least one biomarker to form a kinetic composite value that reflects the change of biomarker presence or concentration; E. Correlating the kinetic composite value to the presence or non-presence of said predefined solid tumor cancer in said individual by comparing the kinetic composite value to a pre-determined cut-off value established with control samples of known predefined solid tumor cancer and benign disease diagnosis; wherein the time period between the first point in time and the second point in time is in the range from 0.5% to 25%, or more preferably in the range from 0.1% to 15%, of a typical tumor volume doubling time of said predefined solid tumor cancer; and the at least one biomarker determined is the same biomarker in each of the biological samples.

26 Claims, 4 Drawing Sheets

(56) References Cited

OTHER PUBLICATIONS

Schmid et al., Observations on the doubling time of prostate cancer. The use of serial prostate-specific antigen in patients with untreated disease as a measure of increasing cancer volume, Cancer, 71(6): 2031-40 (Mar. 15, 1993).
Egawa et al., Impact of Life Expectancy and Tumor Doubling Time on the Clinical Significance of Prostate Cancer in Japan, Jpn. J. Clin. Olcol., 27(6):394-40 (1997).
Kindermann et al., "Influencing of the PSA concentration in serum by physical exercise (especially bicycle riding)", Urologe A., Feb. 2011 (2): 188-96.
Brandle et al., "Serum half-life time determination of free and total prostate-specific antigen following radical prostatectomy—acritical assessment", Urology, Apr. 1999 (4): 722-30.
Kanashiki et al., Volume doubling time of lung cancers detected in a chest radiograph mass screening program: Comparison with CT screening, Oncology Letters, 4:513-516 (2012).
Thompson et al., Assessing prostate cancer risk: Results from the Prostate Cancer Prevention Trial, J. Natl. Cancer Inst., 98(8):529-34 (Apr. 19, 2006).
Thompson et al., "Operating characteristics of prostate-specific antigen in men with an initial PSA level of 3.0 ng/ml or lower", JAMA, Jul. 6, 2005, 294(1): 55-70.
Ewing et al., Germline Mutations in HOXB13 and Prostate-Cancer Risk, The New England Journal of Medicine, 366 (2):141-9 (2012).
Cybulski et al., A Novel Founder CHEK2 Mutation is Associated with Increased Prostate Cancer Risk, Cancer Res, 64(8):2677-2679 (2004).
Cybulski et al., NBS1 Is a Prostate Cancer Susceptibility Gene, Cancer Res, 64(4):1215-1219 (2004).
Magi et al., Contribution of 32 GWAS-Identified Common Variants to Severe Obesity in European Adults Referred for Bariatric Surgery, PLOS ONE, vol. 8, Issue 8:e70735, pp. 1-9 (Aug. 7, 2013).
Hastie et al., The Elements of Statistical Learning, Data Mining, Inference, and Prediction, Springer Series in Statistics, Second Edition 1-764 (Aug. 2008).
Song et al., Whole Milk Intake Is Associated with Prostate Cancer-Specific Mortality among U.S. Male Physicians 1-4, The Journal of Nutrition, 143(2):189-196 (2013, online Dec. 19, 2012).
Eggener SE et al., "Relationship of prostate-specific antigen velocity to histologic findings in a prostate cancer screening program", 2008, 71(6): 1016-1019.
Partin A et al., "Prostate specific antigen in the staging of localized prostate cancer: influence of tumor differentiation, tumor volume and benign hyperplasia", The Journal of Urology, 1990, 143: 747-752.
Minton et al., The use of serial CEA determinations to predict recurrence of colon cancer and when to do second-look operation, Cancer, 42:1422-1427 (1978).
Jäger W et al., "Serial CEA and CA 15-3 Measurements during follow-up of breast cancer patients", Anticancer Research, 2000, 20: 5179-5182.
Hori et al., Mathematical model identifies blood biomarker-based early cancer detection strategies and limitations, Sci. Transl. Med., 3(109):1-19 (via PMC, Aug. 20, 2012).
Klein et al., Blood Biomarker Levels to Aid Discovery of Cancer-Related Single-Nucleotide Polymorphisms: Kallikreins and Prostate Cancer, Cancer Prev Res, 3(5):611-619 (2010).
Zheng et al., A comprehensive association study for genes in inflammation pathway provides support for their roles in prostate cancer risk in the CAPS study, Prostate, 66:1556-1564 (Oct. 1, 2006).
NCBI Database of Single Nucleotide Polymorphisms (dbSNP) https://www.ncbi.nlm.nih.gov/snp. overview dated Feb. 2, 2011.
Nordstrom et al, A Genetic Score Can Identify Men at High Risk for Prostate Cancer Among Men With Prostate-Specific Antigen of 1-3 ng/ml; European Urology, 65:1184-1190 (2014) (online Jul. 19, 2013).
Nordstrom et al: European Urology, Comparison Between the Four-kallikrein Panel and Prostate Health Index for Predicting Prostate Cancer, European Urology, 68:139-146 (2015).
Breiman, Leo, Random Forests, Machine Learning, 45(1):5-32 (2001).
Gudmundsson et al., Genetic Correction of PSA Values Using Sequence Variants Associated with PSA Levels, 2010, Science Translation Medicine, 2(62):62ra92, pp. 1-16 (Dec. 15, 2010).
Nam et al., Single nucleotide polymorphism of the human kallikrein-2 gene highly correlates with serum human kallikrein-2 levels and in combination enhances prostate cancer detection, Journal of Clin. Oncology, 21(12) 2312-2319 (2003).
Amin Al Olama et al., A meta-analysis of genome-wide association studies to identify prostate cancer suspectibility loci associated with aggressive and non-aggressive disease, Human Molecular Genetics, vol. 22, No. 2, p. 408-415 (Oct. 12, 2012).
Official Action from European Application No. 13727408.0, dated Feb. 24, 2016.
Jin et al., Genome-wide association study identifies loci at ATF7IP and KLK2 Associated with Percentage of Circulating Free PSA, Neoplasia, 15(1):95-101 (Jan. 2013).
Anders Bjartell, Genetic Markers and the Risk of Developing Prostate Cancer, European Urology, 60:29-31 (Jan. 1, 2011).
Vickers et al., Reducing Unnecessary Biopsy During Prostate Cancer Screening Using a Four-Kallikrein Panel: An Independent Replication, Journal of Clinical Oncology, vol. 28, No. 15, p. 2493-2498 (May 20, 2010).
Johansson et al., Combining 33 genetic variants with prostate-specific antigen for prediction of prostate cancer: longitudinal study, International Journal of Cancer, 130(1):129-137 (online: Feb. 15, 2011).
Klein et al., Evaluation of Multiple Risk-Associated Single Nucleotide Polymorphisms Versus Prostate-Specific Antigen at Baseline to Predict Prostate Cancer in Unscreened Men, European Urology, 61:471-477 (online: Nov. 9, 2011).
Kader et al., Potential Impact of Adding Genetic Markers to Clinical Parameters in Predicting Prostate Biopsy Outcomes in Men Following an Initial Negative Biopsy: Findings from the REDUCE Trial, European Urology, 62:953-961 (online: May 11, 2012).
Choudhury et al., The Role of Genetic Markers in the Management of Prostate Cancer, European Urology, 62:577-587 (online: Jun. 5, 2012).
Liu et al., A replication study examining three common single-nucleotide polymorphism and the risk of prostate cancer in a Japanese population, The Prostate, 71(10):1023-1032 (2011).
E Möller, H-O Adami et al., "Lifetime body size and prostate cancer risk in a population-based case-control study in Sweden", Cancer Causes and Control, Sep. 19, 2013, 24(12): 2143-2155.
Official Action from corresponding European Application No. 13799501.5, dated Oct. 11, 2016.
Speliotes et al., Association analyses of 249,796 individuals reveal eighteen new loci associated with body mass index, Nature Genetics, 42(11):937-948 (2010).
Ian M. Thompson et al., "Assessing Prostate Cancer Risk: Results from the Prostate Cancer Prevention Trial", Journal or the Nat. Cancer Inst., 98(8), Apr. 19, 2006.
Collette et al., Prostate Specific Antigen: A Prognostic Marker of Survival in Good Prognosis Metastatic Prostate Cancer? (EORTC 30892), European Urology, 44(2):182-189 (2003).
Jin et al., Genome-wide copy-number variation analysis identifies common genetic variants at 20p13 associated with aggressiveness of prostate cancer, Carcinogenesis, 32(7):1057-1062 (May 5, 2011).
Xu et al., Inherited genetic variant predisposes to aggressive but not indolent prostate cancer, Proceedings of the National Academy of Sciences, vol. 107, No. 5, p. 2136-2140 (Feb. 2, 2010).
Johnson et al., Genome-Wide Association Scan Identifies a Risk Locus for Preeclampsia on 2q14, Near the Inhibin, Beta B. Gene, Plos One, vol. 7, No. 3, e33666, p. 1-11 (Mar. 14, 2012).
Piironen, Timo et al., Measurement of Circulating Forms of Prostate-specific Antigen in Whole Blood Immediately after Venipuncture: Implications for Point-of-Care Testing, Clinical Chemistry, vol. 47, No. 4, pp. 703-711 (2001).

(56) References Cited

OTHER PUBLICATIONS

Chissov V.I. ed., Oncology: national leadership, Moscow: GEOTARMedia, pp. 788-798 (2008), and English translation thereof.
Official Action dated Oct. 15, 2018 from corresponding Russian Application No. 2016139491 and English Translation.
Search Report dated Oct. 15, 2018 from corresponding Russian Application No. 2016139491 and English Translation.
English Translation of Office Action dated Mar. 5, 2019 from corresponding Japanese Application No. 2016556777.
Robinson, David et al., Prediction of Survival of Metastatic Prostate Cancer Based on Early Serial Measurements of Prostate Specific Antigen and Alkaline Phosphatase, The Journal of Urology, vol. 179, pp. 117-123 (Jan. 2008).
Official Action dated Jul. 7, 2019 from corresponding Russian Application No. 2016139491/04(063023) with English Translation.

* cited by examiner

METHOD FOR DETECTING A SOLID TUMOR CANCER

FIELD OF THE INVENTION

The present invention relates generally to the detection and identification of various forms of proteins, which have the potential utility as diagnostic markers. In particular, the present invention relates to the repeated test of one or more biomarkers where the variation in time is used for improved detection of solid tumor cancer, such as prostate cancer. More particularly, the present invention relates to the use of at least two biomarker tests collected within a time period corresponding to approximately 0.5-25%, or particularly approximately 0.1% to 15%, of the typical tumor volume doubling time for a predefined type of solid tumor cancer, for improved detection of solid tumor cancer.

BACKGROUND OF THE INVENTION

The measurement of serum prostate specific antigen (PSA) is widely used for the screening and early detection of prostate cancer (PCa). As discussed in the public report "Polygenic Risk Score Improves Prostate Cancer Risk Prediction: Results from the Stockholm-1 Cohort Study" by Markus Aly and co-authors as published in EUROPEAN UROLOGY 60 (2011) 21-28 (which is incorporated by reference herein), serum PSA that is measurable by current clinical immunoassays exists primarily as either the free "non-complexed" form (free PSA), or as a complex with a-lantichymotrypsin (ACT). The ratio of free to total PSA in serum has been demonstrated to significantly improve the detection of PCa. Other factors, like age and documented family history may also improve the detection of PCa further. The measurement of genetic markers related to PCa, in particular single nucleotide polymorphisms (SNP), is an emerging modality for the screening and early detection of prostate cancer. Analysis of multiple PCa related SNPs can, in combination with biomarkers like PSA and general information about the patient, improve the risk assessment through a combination of several SNPs into a genetic score, as described in the patent publication WO2013172779 (which is incorporated by reference herein). The screening and early detection of prostate cancer is a complicated task, and to date no single biomarker has been proven sufficiently good for specific and sensitive mapping of the male population. Therefore, attempts have been spent on combining biomarker levels in order to produce a formula which performs better in the screening and early detection of PCa. The most common example is the regular PSA test, which in fact is an assessment of "free" PSA and "total" PSA. Another such example is the use of combinations of concentrations of free PSA, total PSA, and one or more pro-enzyme forms of PSA for the purpose of diagnosis, as described in WO03100079 (METHOD OF ANALYZING PROENZYME FORMS OF PROSTATE SPECIFIC ANTIGEN IN SERUM TO IMPROVE PROSTATE CANCER DETECTION) which is incorporated by reference herein. The one possible combination of PSA concentrations and pro-enzyme concentrations that may result in improved performance for the screening and early detection of PCa is the phi index. Phi was developed as a combination of PSA, free PSA, and a PSA precursor form [−2]proPSA to better detecting PCa for men with a borderline PSA test (e.g. PSA 2-10 ng/mL) and non-suspicious digital rectal examination, as disclosed in the report "Cost-effectiveness of Prostate Health Index for prostate cancer detection" by Nichol M B and co-authors as published in BJU Int. 2011 Nov. 11. doi: 10.1111/j.1464-410X.2011.10751.x. which is incorporated by reference herein. Another such example is the combination of psp94 and PSA, as described in US2012021925 (DIAGNOSTIC ASSAYS FOR PROSTATE CANCER USING PSP94 AND PSA BIOMARKERS).

There are other biomarkers of potential diagnostic or prognostic value for assessing if a patient suffers from PCa, including MIC-1 as described in the report "Macrophage Inhibitory Cytokine 1: A New Prognostic Marker in Prostate Cancer" by David A. Brown and co-authors as published in Clin Cancer Res 2009; 15(21):OF1-7, which is incorporated by reference herein.

One method used for monitoring of an individual with respect to risk for PCa is to estimate "PSA doubling time", i.e. measuring the PSA value at different time points (at least two) and based on the PSA values calculating the theoretical time it would take to increase the PSA value from one unit to two units. One example of the use of PSA doubling time for individuals with a PCa diagnosis is described in the article "PSA doubling time as a progression criterion in an active surveillance programme for patients with localised prostate cancer." by Thomsen F B, Christensen I J, Brasso K, Røder M A, and Iversen P as published in BJU Int. 2013 Jul. 19. doi: 10.1111/bju.12367, which is incorporated by reference herein. In brief, this report describes the potential use of PSA doubling time as a progression criterion in patients with low-risk prostate cancer managed on active surveillance. A PSA doubling time less than 3 years was considered high risk, 3-5 years was intermediate risk, and PSA doubling time greater than 5 years was considered low risk. Definitive treatment was recommended to high-risk patients and treatment options were discussed with intermediate-risk patients. However, the report concluded that the uncertainty of calculated PSA doubling time during active surveillance results in a significant risk of patients being misclassified according to the progression risk definitions, which subsequently limits its use in the management of patients on active surveillance. Hence, there is room for improvement of methods for monitoring individuals with risk for disease progression.

The current performance of the PSA screening and early detection is approximately a sensitivity of 80% and specificity of 30%. It is estimated that approximately 65% will undergo unnecessary prostate biopsy and that 15-20% of the clinically relevant prostate cancers are missed in the current screening. In the United States alone, about 1 million biopsies are performed every year, which results in about 192 000 new cases being diagnosed. Hence, also a small improvement of diagnostic performance will result both in major savings in healthcare expenses due to fewer biopsies and in less human suffering from invasive diagnostic procedures.

The current clinical practice (in Sweden) is to use total PSA as biomarker for detection of asymptomatic and early prostate cancer. The general cutoff value for further evaluation with a prostate biopsy is 3 ng/mL. However, due to the negative consequences of PSA screening there is no organized PSA screening recommended in Europe or North America today.

All in all, this leads to a large number of individuals being tested regularly for the presence of a variety of cancers, causing stress for the individuals and adding cost to the health care system. It is also possible that individuals with clearly elevated predisposition for a particular cancer disease should have even more frequent doctor's appointments than what is currently common.

It is particularly important to accurately identify aggressive prostate cancer (aPCa) in individuals because the sooner an individual is provided treatment, the greater likelihood of the cancer being cured. The identification of aPCa is however difficult, partly because larger cohorts are required to provide a sufficient number of cases and controls in the development of statistical models. Hence, the availability of predictive models for aPCa is low.

SUMMARY OF THE INVENTION

This invention provides predictive models for the identification of solid tumor cancer, such as prostate cancer (PCa), in particular aggressive prostate cancer (aPCa), through analysis of a biomarker which has been repeatedly quantified in an individual. The present invention is based on the discovery that the combination of diagnostic markers measured at different points in time may improve the ability to detect solid tumor cancer in a general population. This can result in major savings for the society, because cancers that are identified early are more easily treatable. More importantly, the present invention is based on the discovery that a change in the amount or concentration of a biomarker within a short time frame, such as a PCa-related biomarker in an individual, which not necessarily is originating from the presence or growth of a tumor is related to the reduced risk of having solid tumor cancer, such as PCa. This finding has made it possible to present herein an improved and more reliable model for indicating a presence or non-presence of a solid tumor cancer, such as PCa, in an individual.

The current invention is a method to combine information from biomarker values taken at different points in time, to form a risk assessment, in particular for individuals who are not diagnosed with cancer. This risk assessment improves the possibility to determine, in an individualized manner, a suitable time for the next step in the cancer monitoring, wherein a next step could be a new doctor's appointment after 1, 3, 6, 12 or 24 months, or immediate invasive diagnostics (such as referring the individual to a biopsy), or immediate imaging of the individual using for example X-ray imaging, CT-imaging, PET-imaging, SPECT-imaging, MRI-imaging or any other imaging technology suitable for the purpose of identifying a tumor in said individual. The current invention may also be applied for individuals with a cancer diagnosis, for example to determine if the tumor is growing in situations where the progression of the cancer is typically slow.

Accordingly, based on the discoveries of the present disclosure, one aspect of the present disclosure provides a method for indicating the presence or non-presence of a predefined solid tumor cancer in an individual, comprising the steps of:
A. Providing at least one biological sample originating from said individual at a first point in time;
B. Providing at least one biological sample originating from said individual at a second point in time;
C. In said at least two biological samples, measuring a presence or concentration of at least one biomarker related to said predefined solid tumor cancer;
D. Combining data regarding the presence or concentration of the at least one biomarker to form a kinetic composite value that reflects the change of biomarker presence or concentration;
E. Correlating the kinetic composite value to the presence or non-presence of said predefined solid tumor cancer in said individual by comparing the kinetic composite value to a pre-determined cut-off value established with control samples of known predefined solid tumor cancer and benign disease diagnosis;
wherein
the time period between the first point in time and the second point in time is in the range from 0.5% to 25% of a typical tumor volume doubling time of said predefined solid tumor cancer; and
the at least one biomarker determined is the same biomarker in each of the biological samples.

There is also provided a method for indicating the presence or non-presence of a predefined solid tumor cancer in an individual, comprising the steps of
A. In at least two biological samples from an individual originating from a first and a second point in time, measuring a presence or concentration of at least one biomarker from said individual related to said predefined solid tumor cancer;
B. Combining data regarding the presence or concentration of the at least one biomarker to form a kinetic composite value that reflects the change of biomarker presence or concentration;
C. Correlating the kinetic composite value to the presence or non-presence of said predefined solid tumor cancer in said individual by comparing the kinetic composite value to a pre-determined cut-off value established with control samples of known predefined solid tumor cancer and benign disease diagnosis;
wherein
the time period between the first point in time and the second point in time is in the range from 0.5% to 25% of a typical tumor volume doubling time of said predefined solid tumor cancer; and
the at least one biomarker determined is the same biomarker in each of the biological samples.

The step of combining data can also be referred to as a step of generating data to form a kinetic composite value that reflects the change of biomarker presence or concentration. Accordingly, the terms generating and combining may be used interchangeably herein, when referring to any data, values or composite values.

In a preferred aspect of a method described herein, the time period between the first point in time and the second point in time is in the range of about 0.1% to 15% of a typical tumor volume doubling time of said predefined solid tumor cancer; such as about 0.1% to 12.5% of a typical tumor volume doubling time of said predefined solid tumor cancer.

In the above-described method, the predetermined cut-off value preferably discriminates between (i) a highly variable presence or concentration of the at least one biomarker, which is not related to development of the predefined solid tumor cancer, and (ii) a less variable presence or concentration of the at least one biomarker, which is related to development of the predefined solid tumor cancer. Accordingly, in the above-described method the predetermined cut-off value preferably discriminates between (i) a highly variable presence or concentration of the at least one biomarker, which is related to a lower risk of the development of the predefined solid tumor cancer and (ii) a less variable presence or concentration of the at least one biomarker, which is related to a higher risk of the development of the predefined solid tumor cancer.

The method may be applied to a predefined solid tumor cancer, which is selected from the group consisting of bladder cancer, breast cancer, colorectal cancer, endometrial cancer, kidney cancer, renal cell cancer, lung cancer, pancreatic cancer, prostate cancer, and thyroid cancer.

Presently, the method is preferably applied to prostate cancer (PCa), in particular to aggressive prostate cancer (aPCa).

When the method is applied to PCa, such as aPCa, the time period between the first point in time and the second point in time is preferably selected from a range of from 3 days to 6 months, more preferably in a range of about 1 day to 3 months. Time periods of about 3 days to 3 months, about 1 week to 3 months, about 2 weeks to 3 months, about 1 day to 9 weeks, about 3 days to 9 weeks, about 1 week to 9 weeks, about 2 weeks to 9 weeks, about 1 day to 7 weeks, about 3 days to 7 weeks, about 1 week to 7 weeks, or about 2 weeks to 7 weeks, or as disclosed elsewhere herein in the context of PCa, are also useful in the present context.

When the method is applied to PCa, such as aPCa, the at least one biomarker is selected from a group consisting of prostate specific antigen (PSA), free PSA, complexed PSA, pro PSA, intact PSA, total PSA, human prostatic acid phosphatase (PAP), human kallikrein 2 (hK2), early prostate cancer antigen (EPCA), beta-microseminoprotein (MSMB), glutathione S-transferase π (GSTP1), α-methylacyl coenzyme A racemase (AMACR), Macrophage Inhibitory Cytokine 1 (MIC-1), preferably from a group consisting of free PSA, complexed PSA, total PSA, MSMB, MIC-1.

The above-described method may also be applied to ovarian cancer, in which case the presence or concentration of the biomarker CA125 is determined.

Further, the method may be applied to colorectal cancer. Then, the biomarker to be studied is CEA.

Alternatively, the method is applied to breast cancer, in which case the biomarker is CA 15-3.

Further, the method may be applied to pancreatic cancer, and the at least one biomarker is selected from a group consisting of CA 19-9 and CEA.

The above-described method may further comprise:
in said at least two biological samples analyzing a category of SNPs related to said predefined solid tumor cancer (SNPst), by measuring a presence or absence of each of a plurality of SNPst;
Combining data regarding said category of SNPst to form a SNPst composite value representing the SNPst-related risk of developing said predefined solid tumor cancer;
Combining the kinetic composite value and the SNPst composite value to form an overall composite value; and
Correlating said overall composite value to the presence or non-presence of said predefined solid tumor cancer in said individual by comparing said overall composite value to a pre-determined cut-off value established with control samples of known predefined solid tumor cancer and benign disease diagnosis.

The step of combining data regarding said category of SNPst to form a SNPst composite value can also be referred to as a step of generating data regarding said category of SNPst to form a SNPst composite value. Accordingly, as previously mentioned, the terms generating and combining may be used interchangeably herein, when referring to any data, values or composite values.

In the above-described method, the data regarding said at least one biomarker are preferably combined according to a predetermined equation to form said kinetic composite value.

Further, the data regarding said category of SNPs may preferably be combined according to a predetermined equation to form said SNPst composite value.

Also, the kinetic composite value and the SNPst composite value are preferably combined according to a predetermined equation to form said overall composite value.

The present disclosure further relates to a computer program product directly loadable into the internal memory of a digital computer, characterized in that said computer program product comprises software code means for performing at least steps D and E (or at least steps B and C when the method comprises steps A-C only) of the above-described method, such as steps A-E (or steps A-C) of the method.

Preferably, the computer program product further comprises software code means for performing the method including forming a SNPst composite value, forming an overall composite value, and correlating the overall composite value to the presence or non-presence of said predefined solid tumor cancer in said individual by comparing said overall composite value to a pre-determined cut-off value established with control samples of known predefined solid tumor cancer and benign disease diagnosis. The transformation of data in the digital computer generates previously unknown and highly surprising information that was not available until now.

The method may further comprise analyzing a category of SNP related to a biomarker concentration (SNPbm), by measuring a presence or absence of at least one SNPbm; combining data regarding said SNPbm to form a SNPbm composite value, and including said SNPbm composite value in said overall composite value.

The method may in addition or alternatively comprise analyzing a category of SNP related to the Body Mass Index of said individual (SNPbmi), by measuring a presence or absence of at least one SNPbmi; combining data regarding said SNPbmi to form a SNPbmi composite value; and including said SNPbmi composite value in said overall composite value.

In the method, measuring the presence or absence of a SNP may typically comprise measuring the number of alleles of said SNP.

The method may further comprise recommending the individual to change dietary habits, to lose weight, to reach a BMI value below 30, to exercise regularly, and/or to stop smoking, if the kinetic composite value or the overall composite value is greater than the cut-off value.

The method may also encompass collecting the family history regarding the predefined solid tumor cancer, treatment history, physical data and/or concurrent medication from said individual; and wherein said family history, treatment history, physical data and/or concurrent medication are included in the combined data forming said overall composite value.

DETAILED DESCRIPTION OF THE INVENTION

Figure 1:
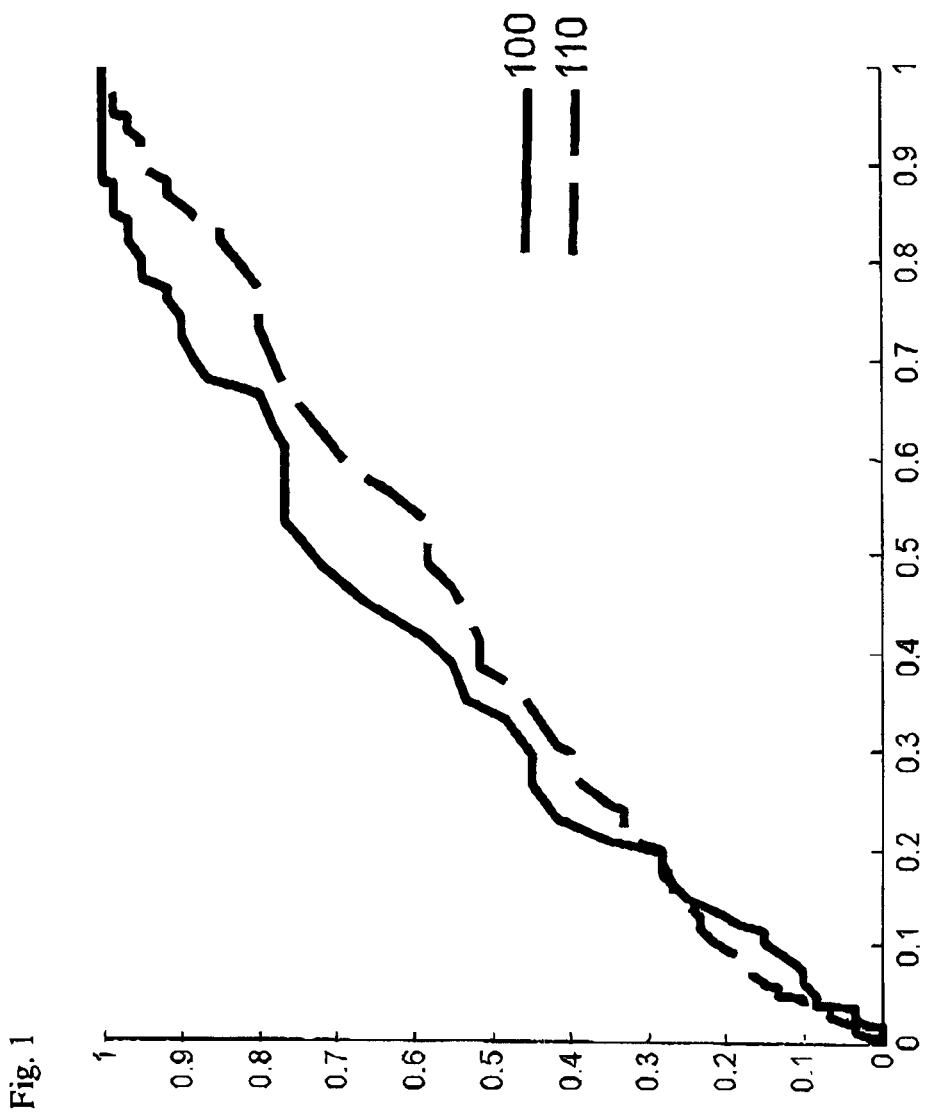
FIG. 1 shows a receiver-operator curve, which illustrates the performance of a diagnostic model using either PSA value or PSA value combined with PSA kinetics.

For the purpose of this application and for clarity, the following definitions are made:

The term biomarker refers to a protein, a part of a protein, a peptide or a polypeptide, which may be used as a biological marker, e.g. for diagnostic purposes.

The term "PSA" refers to serum prostate specific antigen in general. PSA exists in different forms, where the term "free PSA" refers to PSA that is unbound or not bound to another molecule, the term "bound PSA" refers to PSA that is bound to another molecule, and finally the term "total PSA" refers to the sum of free PSA and bound PSA. The term "F/T PSA" is the ratio of unbound PSA to total PSA. There are also molecular derivatives of PSA, where the term "proPSA" refers to a precursor inactive form of PSA and "intact PSA" refers to an additional form of proPSA that is found intact and inactive.

The term kallikrein-like biomarker refers to protein biomarkers belonging to or being related to the kallikrein family of proteins, including but not limited to prostate specific antigen (PSA) in either free form or complexed form, pro PSA (a collection of isoforms of PSA) and in particular the truncated form (−2) pro PSA, intact PSA, human prostatic acid phosphatase (PAP), and human kallikrein 2 (hK2). It is further possible to combine values of biomarkers to form an artificial biomarker, such as forming the quotient of biomarkers. One common and non-limiting example is to use the quotient or ratio of (free PSA)/(total PSA) as an artificial biomarker.

The term "single nucleotide polymorphism" (SNP) refer to the genetic properties of a defined locus in the genetic code of an individual. A SNP can be related to increased risk for PCa, and can hence be used for diagnostic or prognostic assessments of an individual. The Single Nucleotide Polymorphism Database (dbSNP) is an archive for genetic variation within and across different species developed and hosted by the National Center for Biotechnology Information (NCBI) in collaboration with the National Human Genome Research Institute (NHGRI), both located in the US. Although the name of the database implies a collection of one class of polymorphisms only (i.e., single nucleotide polymorphisms (SNP)), it in fact contains a range of molecular variation. Every unique submitted SNP record receives a reference SNP ID number ("rs#"; "refSNP cluster"). In this application, SNP are mainly identified using rs# numbers. Accordingly, within the present application, SNP is used to refer to the range of molecular variation as included in the dbSNP, rather than only single nucleotide polymorphisms. For the purpose of the present application, the terms "SNP" and "SNPs" may be used interchangeably, and may be used to describe the singular and/or the plural of "single nucleotide polymorphism".

The term "body-mass index" (BMI) refers to a heuristic proxy for human body fat based on an individual's weight and height, according to the formula BMI=weight/(height*height), where weight is the weight of an individual expressed in kilograms and height is the height of an individual expressed in meters. A normal healthy BMI value is typically considered to be within the range of 18.5 to 25, and individuals having BMI>30 are typically considered obese.

The term "diagnostic assay" refers to the detection of the presence or nature of a pathologic condition. It may be used interchangeably with "diagnostic method". Diagnostic assays differ in their sensitivity and specificity.

One measure of the usefulness of a diagnostic tool is "area under the receiver—operator characteristic curve", which is commonly known as ROC-AUC statistics. This widely accepted measure takes into account both the sensitivity and specificity of the tool. The ROC-AUC measure typically ranges from 0.5 to 1.0, where a value of 0.5 indicates the tool has no diagnostic value and a value of 1.0 indicates the tool has 100% sensitivity and 100% specificity.

The term "sensitivity" refers to the proportion of all subjects with solid tumor cancer that are correctly identified as such (which is equal to the number of true positives divided by the sum of the number of true positives and false negatives).

The term "specificity" refers to the proportion of all subjects healthy with respect to solid tumor cancer (i.e. not having solid tumor cancer) that are correctly identified as such (which is equal to the number of true negatives divided by the sum of the number of true negatives and false positives).

The term "parameter category" refers to a group or a family of related parameters, such as related biomarkers or related SNPs, which are partly or completely redundant in terms of predictive performance. One example of a parameter category is "SNPs related to a predefined solid tumor cancer" (SNPst). In the prediction models of the present invention, it may be sufficient to have measurement results (data) for a subset of the members of each category, so as to make each category represented in the prediction model, albeit using only a subset of the members of the respective categories. The term "parameter category" is sometimes referred to as only "category" in the present application.

The term "composite value" refers to the combination of data related to a parameter category into a representative value for said parameter category. The combination of data can typically be performed according to one or more predetermined equations. A composite value is the output of the combination of data according to one or more predetermined equations. The different equations are applicable for different measurement results (i.e. data), depending on for which subsets of the members of the parameter category that data are available. One non-limiting example of a method to form a composite value for a particular parameter category is to use the average of the available results for the members of said category. The term "composite value" is sometimes referred to as "score" in the present application. One non-limiting example of a composite value is "biomarker composite value". Another non-limiting example of a composite value is "genetics composite value" (or "genetic score"), and more specifically "SNP composite value".

The term "kinetic composite value" is a special case of a composite value, wherein the kinetic composite value includes data from the same biomarker at different points in time, so as to provide a measure of the change of biomarker property over time.

Cancer is a broad group of diseases involving unregulated cell growth. In cancer, cells divide and grow uncontrollably, forming malignant tumors, and invading nearby parts of the body. The term "solid tumor cancer" is defined as a cancer disease wherein the malignant tumor is present at a distinct location. Bladder cancer, breast cancer, colon and rectal cancer (colorectal cancer), endometrial cancer, kidney (renal cell) cancer, lung cancer, pancreatic cancer, prostate cancer, and thyroid cancer are non-limiting examples of different types of solid tumor cancers. Leukemia is an example of a cancer that is not a solid tumor cancer.

Herein, the term "a predefined solid tumor cancer" signifies a type of solid tumor cancer. Different types of solid tumor cancers are exemplified above.

The term prostate cancer (PCa) refers to solid tumor cancer located in the prostate.

The term aggressive prostate cancer (aPCa) refers to a more serious condition than the average prostate cancer disease. aPCa can be defined in different ways, including but not limited to (a) prostate cancer of Gleason Score 7 or higher, (b) prostate cancer in tumor stage three or greater, (c) prostate cancer in an individual having a PSA value greater than 10 ng/mL, (d) an individual having an increasing PSA value (doubling time less than one year), and (e) computer assisted image analysis (e.g. positron emission tomography (PET) or single photon emission computerized tomography (SPECT) or computerized x-ray tomography (CT) or magnetic resonance imaging (MRI) or ultrasound imaging or any other computer assisted image analysis) indicating a tumor size in the higher quartile of the patient population.

The term medical history refers to information related to historic examinations, diagnoses and/or therapy for any cancer disease. One non-limiting example of medical history is if a subject has been examined for the presence of PCa previously through biopsy of the prostate.

The present invention provides diagnostic methods to aid in estimating, detecting and/or determining the presence or non-presence of solid tumor cancer, such as aggressive prostate cancer, in a subject. The present invention can, if desired, be tailored to defined subpopulations in order to increase the performance and the usefulness of the invention within said subpopulation. One non-limiting example of a defined subpopulation is individuals having high body-mass index (BMI), for example BMI>30.

The basic principle of the invention is the use of multiple measurements at different points in time of a biomarker in a manner that improves the quality of the diagnosis of a predefined solid tumor cancer for an individual. The method can be described as a step-wise procedure, essentially according to the following:

Obtaining a first biological sample from said patient at a first point in time.
In said first biological sample, quantifying the presence or concentration of at least one defined biomarker.
Optionally collecting the family history regarding a predefined solid tumor cancer from said patient.
Optionally collecting patient physical data, such as weight, BMI, age and similar.
Obtaining a second biological sample from said patient at a second point in time, which occurs within a time period corresponding to approximately 0.5-25% of the typical tumor volume doubling time for the predefined solid tumor cancer.
In said second biological sample, quantifying the presence or concentration of at least one defined biomarker.
Combining biomarker data from the at least two points in time to form a kinetic composite value for the use in the detection of early prostate cancer.
Determining by using said kinetic composite value, alone or in combination with further data, if the patient is likely to suffer from the predefined solid tumor cancer.

The method may also be described in the following manner:

Quantifying the presence or concentration of at least one defined biomarker in a first biological sample from a patient said first biological sample originating from a first point in time.
Optionally collecting the family history regarding a predefined solid tumor cancer from said patient.
Optionally collecting patient physical data, such as weight, BMI, age and similar.
Quantifying the presence or concentration of at least one defined biomarker in a second biological sample from said patient said second biological sample originating from a second point in time, which time period between a first point in time and a second point in time corresponds to approximately 0.5-25% of the typical tumor volume doubling time for the predefined solid tumor cancer.
In said second biological sample, quantifying the presence or concentration of at least one defined biomarker.
Combining biomarker data from the at least two points in time to form a kinetic composite value for the use in the detection of early prostate cancer.
Determining by using said kinetic composite value, alone or in combination with further data, if the patient is likely to suffer from the predefined solid tumor cancer.

In a preferred aspect, the time period between the first point in time and the second point in time is in the range of about 0.1% to 15% of a typical tumor volume doubling time for the predefined solid tumor cancer, such as about 0.1% to 12.5% of a typical tumor volume doubling time for the predefined solid tumor cancer.

Collecting biological samples from a patient includes, but is not limited to plasma, serum and urine. Biological samples include, but are not limited to, plasma, serum and urine samples.

The quantification of presence or concentration of biomarkers in a biological sample can be made in many different ways. One common method is the use of enzyme linked immunosorbent assays (ELISA) which uses antibodies and a calibration curve to assess the presence and (where possible) the concentration of a selected biomarker. ELISA assays are common and known in the art, as evident from the publication "Association between saliva PSA and serum PSA in conditions with prostate adenocarcinoma." by Shiiki N and co-authors, published in Biomarkers. 2011 September; 16(6):498-503, which is incorporated by reference herein. Another common method is the use of a microarray assay for the quantification of presence or concentration of biomarkers in a biological sample. A typical microarray assay comprises a flat glass slide onto which a plurality of different capture reagents (typically an antibody) each selected to specifically capture one type of biomarker is attached in non-overlapping areas on one side of the slide. The biological sample is allowed to contact, for a defined period of time, the area where said capture reagents are located, followed by washing the area of capture reagents. At this point, in case the sought-after biomarker was present in the biological sample, the corresponding capture reagent will have captured a fraction of the sought-after biomarker and keep it attached to the glass slide also after the wash. Next, a set of detection reagents are added to the area of capture reagents (which now potentially holds biomarkers bound), said detection reagents being capable of (i) binding to the biomarker as presented on the glass slide and (ii) producing a detectable signal (normally through conjugation to a fluorescent dye). It is typically required that one detection reagent per biomarker is added to the glass slide. There are many other methods capable of quantifying the presence or concentration of a biomarker, including, but not limited to, immunoprecipitation assays, immunofluorescence assays, radio-immuno-assays, and mass spectrometry using matrix-assisted laser desorption/ionization (MALDI), to mention a few examples.

Accordingly, there is also provided herein a diagnostic kit or product for use in performing a method as defined herein, comprising means for measuring biomarker concentration/presence and change and/or means for quantifying/determining the presence of SNPs and/or computational means for determining values and optionally instructions for use. Other suitable means for performing said method as mentioned herein may also be useful in a kit.

The step of combining biomarker data from the at least two points in time to form a kinetic composite value can be conducted in many different ways. Typically, the biomarker data refers to an at least partly overlapping set of biomarkers being quantified at two different points in time, making it possible to calculate the change of the concentration of a particular biomarker. One possible non-limiting method for estimating the change is to define a range of accepted time intervals for the two points in time when samples are obtained, and also to define a level for what is to be considered a small change. Any change (increasing or decreasing) greater than the small change level is then considered a confirmed change of biomarker concentration. A change is also referred to herein as a highly variable presence or concentration of said at least one biomarker. A less variable presence or concentration of the at least one biomarker is used herein to refer to no change in the presence or concentration of said at least one biomarker.

As a practical, non-limiting example of this method, it is possible to define that the two samples must be taken in, or originate from, the time span of 10 days to 30 days, and that any biomarker concentration change of less than 10% is considered a small change. Another possible non-limiting method for estimating the change is to calculate the average change per unit time. Hence, if two samples are obtained 10 days apart, the first sample results in a biomarker concentration of 10 units and the second sample results in 20 units, the change is 1 unit/day.

The definition of how "change of biomarker concentration" is calculated will have an impact on the maximum time that can be considered as "short time". If, for example, a small variation of biomarker concentration is considered as a change (such as 3% change in any direction), then the "short time" has to be only 1-4% of the tumor doubling time because otherwise tumor growth alone may cause such a change. If, as another example, a larger variation of biomarker concentration is required to consider a change to have happened (such as 30% change in any direction), then the "short time" can be much longer (up to 25-30% of the doubling time), because tumor growth alone will take longer time to approach such a large change.

In accordance therewith, it is possible to set up the characteristics of a method as disclosed herein by firstly defining how a "change in biomarker concentration" is to be calculated. This definition may then be a guidance for determining the suitable time period between the origin of the samples (such as between the first and the second sample). Examples of what may be considered a change in a biomarker concentration as well as suitable time periods are further described herein. This further means that the generic range of suitable time periods for the present invention is more extensive than, but in the vicinity of, the time periods described herein.

In relation thereto, the following scenarios may be envisaged:

When the concentration or presence of a biomarker, such as a PCa-related biomarker, in a biological sample originating from a first point in time is elevated compared to a concentration or presence in a normal population and the concentration or presence of a biomarker, such as a PCa-related biomarker, in a biological sample originating from a second point in time is approximately constant in comparison with the biological sample obtained at a first point in time, this is indicative of a higher risk for a solid tumor cancer, such as PCa;

When the concentration or presence of a biomarker, such as a PCa-related biomarker, in a biological sample originating from a first point in time is elevated compared to concentration or presence in a normal population and the concentration or presence of a biomarker, such as a PCa-related biomarker, in a biological sample originating from at a second point in time has changed (either increased or decreased) in comparison with the biological sample originating from a first point in time, this is indicative of a lower risk for a solid tumor cancer, such as PCa.

Depending on the risk level as estimated using the generated kinetic biomarker value, alone or in combination with the absolute biomarker concentration for the first and or the second point in time, the resulting consequence for the individual under investigation vary: for low risk estimates the consequence may be to recommend a new test within 3-10 years, for intermediate risk estimate the consequence may be to recommend a new test within 1-3 years, and for high risk estimates the consequence may be to recommend said individual to immediately proceed to confirmatory diagnostic procedures, such as imaging or biopsy procedures.

As mentioned in the above, a "change" in biomarker concentration may be differently defined.

The rationale for assessing the same biomarker more than once separated in time is to determine if said biomarker changes its value. Different biological processes have different time scales. Prostate cancer is for example typically a slow process which develops over months or even years. Hence, a prostate cancer tumor will not likely change its properties to any significant extent during the course of a few days, a few weeks, or even a few months. If an elevated PSA value is observed for an individual, and the elevated PSA value stays approximately constant during a relatively short term or time period (further defined below), then it is likely that the tumor is the cause of the elevated PSA value. If, on the other hand, the PSA value changes more than 5%, or changes more than 10%, or even changes more than 15-25%, or 15-30% during a relatively short term or time period, then there is reason to believe that other biological processes are the cause of the elevated PSA value. Inflammation and physical exercise are two examples of non-cancer related processes that can cause an elevated PSA value in the short term. Furthermore, different types of medication may affect the short term PSA value, such as the use of non-steroidal anti-inflammatory drugs (NSAID) to treat inflammation, or the use of statins to treat high blood pressure, to mention two non-limiting examples. Similar reasoning can be applied to other biomarkers that are connected to prostate cancer. In general, many solid tumor cancers are slow-growing, including but not limited to breast cancer, colorectal cancer, ovarian cancer and lung cancer. Hence, short term changes of the presence or concentration of relevant biomarkers related to other slow-growing solid tumor cancers may also be indicative of whether an elevated biomarker value is related to a different condition or process than cancer.

As a non-limiting example, for the PCa-related biomarker PSA, an approximately 10% difference or more between the concentration or presence of a biomarker in a first and a second biological sample originating from a first and a second point in time may be defined as a change. In accordance with the above, a 10% change or less in biomarker concentration is then regarded as an approximately constant concentration or presence (no change) indicating a higher risk of developing PCa. A more than 10%, decrease or increase, is an indication of a lower risk for PCa (change). In the context of defining change as more than 10% increase or decrease, a suitable time period between the first point in time and the second point in time is in the range of 1 day to 7 weeks, 3 days to 7 weeks, or 1 week to 7 weeks. A different definition of what is considered change will result in a different suitable time period.

Further, the present method is particularly useful for cases where the biomarker concentration of at least one of the samples taken during a relatively short term is considered low according to clinical practice.

Changes in the presence or concentration of a cancer-related biomarker should be seen in the light of the typical development of a predefined solid tumor cancer. One parameter that reflects the development of a solid tumor cancer is the tumor volume doubling time. The doubling time indicates how rapid, i.e. aggressive and serious, the development of the solid tumor cancer is, and this parameter is highly variable between different cancers. Thus, the practical meaning of "a short term change" may differ depending on which cancer type the present method is applied on.

Herein, the expression "a short term", in the context of change in the concentration of a cancer-related biomarker, is taken to mean a maximum of 30%, more preferably a maximum of 25%, of the typical time for doubling of the volume of a predefined solid tumor cancer. More particularly, a "short term" is in the range of from 0.1% to 30%, preferably in the range from 0.5% to 25%, or more preferably in the range from 0.1% to 15%, such as about 0.1% to 12.5%, about 0.4% to 9%, or about 1% to 7%, or as disclosed elsewhere herein in this context, of the typical time for doubling of the volume of a solid tumor cancer, provided that the "short term" is at least 1 day, meaning that two consecutive samples should not be taken on, or originate from, the same day; at least 12 h (one night) should pass between the collection, or origin, of two consecutive samples. Other examples of suitable "short terms" are in the range of about 0.5% to 15%, 1% to 15%, 2% to 15%, 0.5% to 12.5%, 1% to 12.5%, 2% to 12.5%, 0.5% to 7%, 1% to 7% or 2% to 7%, or as disclosed elsewhere herein, of the typical time for doubling of the volume of a solid tumor cancer. More particularly, a "short term" is a fraction of the typical time for doubling of the volume of a solid tumor cancer equaling 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, provided that the "short term" is at least 1 day, meaning that two consecutive samples should not be taken on the same day; at least 12 h (one night) should pass between the collection of two consecutive samples. Herein, the expression "time of doubling of the volume of a predefined solid tumor cancer" may alternatively be referred to as the tumor volume doubling time for a predefined solid tumor cancer, or as the doubling time of the tumor volume for a predefined solid tumor cancer.

The reason for relating the time between two different samples to the typical doubling time of the volume of the solid tumor cancer is as follows. Assuming a constant cell cycle time, the tumor will grow 22% in volume during the first 30% of the typical doubling time, or 19% in volume during the first 25% of the typical doubling time. When further assuming that the tumor volume is related to the biomarker concentration in the blood stream, it is expected that the biomarker concentration is changing less than 22% during the first 30% of the typical doubling time, or 19% during the first 25% of the doubling time. This also means that biomarker concentration changes greater than 22% during the first 30% of the typical doubling time, or 19% during the first 25% of the doubling time, is either due to an unusually aggressive tumor disease, or is due to some other biological reason. In the case where the biomarker concentration in at least one of the consecutive samples is low, the likelihood of aggressive cancer is typically low, leaving other biological processes as the most probable cause for the observed variation. The same reasoning can be applied to any fraction of doubling time.

Prostate cancer is known to be a disease with slow progression, as discussed in the report "Observations on the doubling time of prostate cancer. The use of serial prostate-specific antigen in patients with untreated disease as a measure of increasing cancer volume", by Schmid and co-authors as published in Cancer, 1993 Mar. 15; 71(6): 2031-40, which is incorporated by reference herein. According to this report, the time for doubling of the tumor volume exceeds 24 months in a majority of the prostate cancers studied. Another report related to tumor volume in prostate cancer discloses that a 2-year doubling time for prostate cancer can be considered aggressive, while 3- and 4-year doubling times represent the typical growth rate of most diagnosed prostate cancers ("Impact of Life Expectancy and Tumor Doubling Time on the Clinical Significance of Prostate Cancer in Japan" by Egawa and co-authors, Jpn. J. Clin. Oncol. (1997) 27 (6): 394-40; incorporated by reference herein).

In the case of PCa, the typical doubling time is thus approximately 24 months. It is therefore expected that during 25% of the doubling time (i.e. approximately 6 months) the biomarker concentration is expected to increase approximately 19% due to tumor growth. When looking at 12.5% of the doubling time (approximately 3 months) the biomarker concentration is expected to increase 9% due to tumor growth. Therefore, for individuals with a total PSA value less than approximately 10 ng/mL and with a change of PSA value greater than 19% within a period of time shorter than 6 months, the most likely cause for the change of PSA value is non-tumor related. In the same way, a total PSA value changing more than 9% within a period of time shorter than 3 months is probably not related to tumor biology.

In accordance therewith, the present invention utilizes the variation of a biomarker such as a PCa-related biomarker using a definition of variation that is not solely dependent upon the expected increase of biomarker due to actual tumor growth during the time period between the origin of the two samples. This is in sharp contrast to seemingly similar methods such as PSA velocity or estimating PSA doubling time, where the biomarker concentration is assumed to originate from tumor volume and the velocity or doubling time implicitly represents tumor volume. This is further seen in the seemingly contradictory findings that short term biomarker increase is indicative of reduced risk for cancer, while a long term increase most probably is indicative of increased risk for cancer. This fact is also further explained herein.

It is known that the concentration or presence of some biomarkers, such as PCa-related biomarkers, in an individual is not only dependent on the presence or the growth of a tumor but is also dependent on other biological processes. The surprising finding of this invention is that the use of two biological samples originating from within a short time interval is capable of separating elevated biomarker concentration due to cancer from elevated biomarker concentration due to other biological processes thereby providing for that the risk assessment for the individual can be greatly improved. Hence, this is illustrated herein by a unique and reliable risk assessment method for the development of a predefined solid tumor cancer, particularly PCa, in an individual. The method makes it possible to reduce the time period between the two first biological samples significantly while still obtaining an accurate indication of the health status of an individual. Such a method also reduces the need for early invasive biopsies in patients presenting a high biomarker concentration or presence in the first stages of a diagnostic procedure by providing an alternative risk measurement method for a predefined solid tumor cancer, such as PCa.

The shorter limit of the time between two tests is related to multiple factors, including serum half-life of the biomarker and duration of common non-tumor related biological causes for elevated biomarker levels. In the case of PSA value, it is known that physical exercise, especially bicycle riding, increases the PSA value during approximately two days, as disclosed by Kindermann and co-authors in the report "Influencing of the PSA concentration in serum by physical exercise (especially bicycle riding)", published in Urologe A. 2011 February; 50(2):188-96, which is incorporated by reference herein). The biological half-life of PSA in the blood stream after radical prostatectomy is biphasic with an initial rapid decrease to half the one component within approximately two hours followed by a second phase slow decrease with a half-life of approximately 2.7 days, all according to the report "Serum half-life time determination of free and total prostate-specific antigen following radical prostatectomy—a critical assessment." by Brandle and co-authors as published in Urology, 1999 April; 53(4):722-30, which is incorporated by reference herein. Put together, physical exercise induces a fast release of PSA, and it takes the body at least two days to eliminate the released PSA from the body. The fast release of PSA leads to a change (increase) in PSA concentration that could be detected by comparing the PSA concentration in two samples taken during the same day, within 12 hours. However, the elimination of PSA from the body is a slower process, and thus a substantial change (decrease) in PSA concentration may not be detected if the two samples are taken during the same day. Thus, when PSA is the biomarker to be tested, the shortest time between two samples should be at least 1 day, preferably 2, 3 or 4 days.

According to the definition above, a short term or time period is in the range of from 0.1% to 30%, preferably in the range from 0.5% to 25%, 0.1% to 15%, or as disclosed elsewhere herein, of the typical time for doubling of the volume of a solid tumor cancer, provided that the "short term" is at least 1 day. Accordingly, in the context of prostate cancer, a short term consequently corresponds to a time period in the range of 1 day to 8 months, preferably in the range of 3 days to 6 months, but even more preferably in the range from about 1 day to 3.5 months, about 1 day to 3 months, about 3 days to 9 weeks, or about 1 week to 7 weeks, or as disclosed elsewhere herein in the context of prostate cancer. More particularly, in a method for indicating a presence or non-presence of a prostate cancer in an individual, the time period between the collection, or origin, of two consecutive biological samples is in the range of 1 day, 2 days, 3 days, 4 days, 5 days, 1 week, 2 weeks, 3 weeks, 1 month, 1.5 months, 2 months, 2.5 months, 3 months, 3.5 months, 4 months, 4.5 months, 5 months, 5.5 months, 6 months, 7 months, or 8 months, preferably in the range of 3 days, 4 days, 5 days, 1 week, 2 weeks, 3 weeks, 1 month, 1.5 months, 2 months, 2.5 months, 3 months, 3.5 months, 4 months, 4.5 months, 5 months, 5.5 months, or 6 months. Within such a short term or time period, the tumor biology does not change to any great extent. Consequently, if the concentration of a PCa-related biomarker is highly variable during such a short term, it is probably due to other conditions or processes than a development of the prostate cancer tumor or a change in the tumor biology.

As previously mentioned, the definition of how a "change of biomarker concentration" is calculated will have an impact on the maximum time that can be considered as "short time" or "time period" as mentioned herein. Non-limiting examples of "short times" or "time periods" are shown in the experimental section, particularly illustrating the usefulness of time periods from one or a few days up to around 3 months between the origins of the first and the second biological sample.

For lung cancer, the typical tumor volume doubling time is approximately 160 days as reported in "Volume doubling time of lung cancers detected in a chest radiograph mass screening program: Comparison with CT screening." by Kanashiki and co-authors as published in Oncol Lett. 2012 September; 4(3):513-516 (which is incorporated by reference herein). This means that a short term in the context of lung cancer disease is in the order of 1-50 days, such as 1, 2, 3, 4, 5, 10, 15, 20, 25, 30, 35, 40, 45, or 50 days, preferably from 1-40 days.

Suitable biomarkers for diagnosing PCa, such as aPCa, include, but are not limited to, prostate specific antigen (PSA) in either free form or complexed form, pro PSA (a collection of isoforms of PSA) and in particular the truncated form (−2) pro PSA, intact PSA, total PSA, human prostatic acid phosphatase (PAP), human kallikrein 2 (hK2), early prostate cancer antigen (EPCA), Prostate Secretory Protein (PSP94; also known as beta-microseminoprotein and MSMB), glutathione S-transferase π (GSTP1), and α-methylacyl coenzyme A racemase (AMACR). Related biomarkers, which may be useful for improving the diagnostic accuracy of the method includes Macrophage Inhibitory Cytokine 1 (MIC-1; also known as GDF-15).

Suitable biomarkers for other types of solid tumor cancers include, but are not limited to the following.
Ovarian cancer: CA-125 antigen (CA125 or CA-125)
Colorectal cancer: carcinoembryonic antigen (CEA)
Breast cancer: Mucin-1, also known as CA 15-3 antigen
Pancreatic cancer: CA 19-9 antigen, CEA As has been discussed previously, the assessment of the performance of PCa screening efficiency is difficult. Although the ROC-AUC characteristics provide some insight regarding performance, additional methods are desirable. One alternative method for assessing performance of PCa screening is to calculate the percentage of positive biopsies at a given sensitivity level and compare the performance of screening using PSA alone with any novel method for screening. This however requires that the performance of PSA is accurately defined.

One example of an assessment performance of PSA screening has been disclosed by IM Thompson and co-authors in the report "Assessing prostate cancer risk: results from the Prostate Cancer Prevention Trial." as published in J Natl Cancer Inst. 2006 Apr. 19; 98(8):529-34 (which is incorporated by reference herein). In this report, prostate biopsy data from men who participated in the Prostate Cancer Prevention Trial (PCPT) was used to determine the sensitivity of PSA. In total, 5519 men from the placebo group of the PCPT who underwent prostate biopsy, had at least one PSA measurement and a digital rectal examination (DRE) performed during the year before the biopsy, and had at least two PSA measurements performed during the 3 years before the prostate biopsy was included. This report discloses that when using a PSA value of 3 ng/mL as a cutoff, about 41% of the high-grade cancers (i.e. cancers with Gleason score 7 or above) will be missed.

A second analysis using the same study population has been disclosed by IM Thompson and co-authors in "Operating characteristics of prostate-specific antigen in men with an initial PSA level of 3.0 ng/ml or lower" as published in JAMA. 2005 Jul. 6; 294(1):66-70 (which is incorporated by reference herein). In this report, the authors present an estimate of the sensitivity and specificity of PSA for all prostate cancer, Gleason 7+ and Gleason 8+. When using 3.1 ng/mL as PSA cut off value for biopsy a sensitivity of 56.7% and a specificity of 82.3% for Gleason 7+ tumors was estimated. In this report the authors concluded that there is no cut point of PSA with simultaneous high sensitivity and high specificity for monitoring healthy men for prostate cancer, but rather a continuum of prostate cancer risk at all values of PSA. This illustrates the complication with PSA as a screening test while still acknowledging the connection of PSA with prostate cancer.

One inevitable consequence of the difficulties in obtaining accurate and comparable estimates of the predictive performance of any given diagnostic or prognostic model in the screening of PCa is that when calculating the relative improvement of a novel method as compared to using PSA alone, the calculated relative improvement will vary depending on many factors. One important factor that influences the calculated relative improvement is how the control group (i.e. known negatives) is obtained. Since it is unethical to conduct biopsies on subjects where there are no indications of PCa, the control group will be selected with bias. Thus, the relative improvement of a novel method will depend on how the control group was selected, and there are multiple fair known methods to select control groups. Any reported estimated improvement must therefore be seen in the light of such variance. To the best of our experience, we estimate that if the relative improvement of a novel method is reported to be 15% as compared to the PSA value alone using one fair known method for selecting the control group, said novel method would be at least 10% better than the PSA value alone using any other fair known method for selecting the control group.

To become used in a widespread manner in society, the performance of a screen must meet reasonable health economic advantages. A rough estimate is that a screening method performing about 15% better than current PSA tests (i.e. avoiding 15% of the unnecessary biopsies) at the same sensitivity level, i.e. detecting the same number of prostate cancers in the population, would have a chance of being used in a widespread manner in the current cost level of public health systems. However, for defined subpopulations of individuals a novel screening method may have economic advantages also for smaller improvements as compared to the PSA value performance. It is noted that even though significant efforts have been put on finding a combined model for the estimation of PCa risk (as exemplified in several of the cited documents in this patent application), no such combined method is currently in regular use in Europe. Thus, previous known multiparametric methods do not meet the socioeconomic standards to be useful in modern health care. The method of the current invention has better performance than previously presented combined methods and meet the socioeconomic performance requirements to at all be considered by a health care system.

One possible method for obtaining a screening method for aPCa meeting the requirements for widespread use is to combine information from multiple sources. From an overview level, this comprises combining values obtained from biomarker analysis (e.g. PSA values), the change of biomarker levels within a defined period of time, genetic profiles (e.g. the SNP profile), family history, and other sources. The combination as such has the possibility to produce a better diagnostic statement than any of the included factors alone. Attempts to combine values into a multiparametric model to produce better diagnostic statements have been disclosed in the past, as described elsewhere in the current application.

Any screening method for solid tumor cancer will have one or more cutoff values, or threshold values, to determine if an individual has higher or lower risk for the solid tumor cancer. The selection of such one or more cutoff value will depend on regional factors, such as the capacity of heath care providers to treat the cancer type, the reimbursement system, and the overall life expectancy in the region. This means that there is no generic method to determine optimal cutoff value(s). In most countries, the desired approach would be to select cutoff value(s) that either result in a sensitivity in the approximate region 0.55-0.7 with specificity of at least 0.6 or in a sensitivity in the approximate region 0.7-0.9 with specificity of at least 0.2.

In cases where the kinetic composite value is combined with a composite value representing the genetic status of an individual, the quantification of genetic status through the analysis of a biological sample typically involves MALDI mass spectrometry analysis based on allele-specific primer extensions, even though other methods are equally applicable. This applies to any type of genetic status, i.e. both SNPs related to solid tumor cancer and SNPs related to biomarker expression. An example of how genetic status can be transformed into a composite value and further be combined with other sources of information has been disclosed in the above-referenced patent application WO2013172779.

SNPs related to solid tumor cancer are herein exemplified by SNPs related to PCa, which include, but are not limited to rs12621278 (Chromosome 2, locus 2q31.1), rs9364554 (Chromosome 6, locus 6q25.3), rs10486567 (Chromosome 7, locus 7p15.2), rs6465657 (Chromosome 7, locus 7q21.3), rs2928679 (Chromosome 8, locus 8p21), rs6983561 (Chromosome 8, locus 8q24.21), rs16901979 (Chromosome 8, locus 8q24.21), rs16902094 (Chromosome 8, locus 8q24.21), rs12418451 (Chromosome 11, locus 11q13.2), rs4430796 (Chromosome 17, locus 17q12), rs11649743 (Chromosome 17, locus 17q12), rs2735839 (Chromosome 19, locus 19q13.33), rs9623117 (Chromosome 22, locus 22q13.1), and rs138213197 (Chromosome 17, locus 17q21)

Suitable SNPs related to PCa further include, but are not limited to rs11672691, rs11704416, rs3863641, rs12130132, rs4245739, rs3771570, rs7611694, rs1894292, rs6869841, rs2018334, rs16896742, rs2273669, rs1933488, rs11135910, rs3850699, rs11568818, rs1270884, rs8008270, rs4643253, rs684232, rs11650494, rs7241993, rs6062509, rs1041449, and rs2405942.

Suitable SNPs related to PCa further include, but are not limited to rs138213197 as described in the report "Germline mutations in HOXB13 and prostate-cancer risk." by Ewing CM and co-authors as published in N Engl J Med. 2012 Jan. 12; 366(2):141-9 (which is incorporated by reference herein), 1100delC (22q12.1) and I157T (22q12.1) as described in the report "A novel founder CHEK2 mutation is associated with increased prostate cancer risk." by Cybulski C and co-authors as published in Cancer Res. 2004 Apr. 15; 64(8):2677-9 (which is incorporated by reference herein), and 657del5 (8q21) as described in the report "NBS1 is a prostate cancer susceptibility gene" by Cybulski C and co-authors as published in Cancer Res. 2004 Feb. 15; 64(4):1215-9 (which is incorporated by reference herein). It is possible to define a parameter category as "SNP related to PCa" which includes SNP related to PCa. Suitable members include (but are not limited to) the SNPs listed above. A subset of the members of this category would be sufficient to represent the category as such in a predictive model.

SNPs suitable to study in the context of PCa further encompass SNPs related to other processes than PCa. Such SNPs include, but are not limited to rs3213764, rs1354774, rs2736098, rs401681, rs10788160, rs11067228, all being related to the expression level of PSA. It is possible to define a parameter category as "SNP related to concentration of PSA" or "SNP related to expression level of PSA", which includes SNP related to the concentration or expression level of PSA. A subset of the members of this category would be sufficient to represent the category as such in a predictive model. The SNP rs3213764 and rs1354774 relate particularly to the expression level of free PSA.

Suitable SNPs related to other processes than PCa further include, but are not limited to rs1363120, rs888663, rs1227732, rs1054564, all being related to the expression level of the inflammation cytokine biomarker MIC1. It is possible to define a parameter category as "SNP related to concentration of MIC1" or "SNP related to expression level of MIC1" which includes SNP related to the concentration or expression level of MIC1. A subset of the members of this category would be sufficient to represent the category as such in a predictive model.

It is possible to define a parameter category as "SNP related to PCa biomarker concentration" or "SNP related to PCa biomarker expression level" which includes SNP related to the concentration or expression level of relevant biomarkers such as Prostate-specific antigen (PSA) in either free form or complexed form, pro PSA (a collection of isoforms of PSA) and in particular the truncated form (−2) pro PSA, intact PSA, human prostatic acid phosphatase (PAP), human kallikrein 2 (hK2), early prostate cancer antigen (EPCA), Prostate Secretory Protein (PSP94; also known as beta-microseminoprotein and MSMB), glutathione S-transferase π (GSTP1), α-methylacyl coenzyme A racemase (AMACR), and Macrophage Inhibitory Cytokine 1 (MIC-1; also known as GDF-15). A subset of the members of this category would be sufficient to represent the category as such in a predictive model.

Suitable SNPs related to other processes than PCa further include, but are not limited to rs3817334, rs10767664, rs2241423, rs7359397, rs7190603, rs571312, rs29941, rs2287019, rs2815752, rs713586, rs2867125, rs9816226, rs10938397, and rs1558902 all being related to the BMI of an individual. Other suitable SNP related to BMI are disclosed in the report "Contribution of 32 GWAS-identified common variants to severe obesity in European adults referred for bariatric surgery" by Magi and co-authors as published in PLoS One. 2013 Aug. 7; 8(8):e70735 (which is incorporated by reference herein). It is possible to define a parameter category as "SNP related to expression level of BMI" which includes SNP related to the BMI of the individual. A subset of the members of this category would be sufficient to represent the category as such in a predictive model.

A preferred collection of SNPs to be used in the assessment of the presence or non-presence of prostate cancer, such as aggressive prostate cancer, in a subject is rs582598, rs439378, rs2207790, rs1046011, rs10458360, rs7525167, rs10489871, rs7529518, rs4245739, rs4512641, rs10178804, rs11900952, rs1873555, rs10191478, rs6755901, rs6545962, rs721048, rs2710647, rs12612891, rs2028900, rs1009, rs12233245, rs6760417, rs10496470, rs10199796, rs12475433, rs16860513, rs12151618, rs3765065, rs13017302, rs12988652, rs871688, rs749264, rs3771570, rs4346531, rs6770955, rs12637074, rs2660753, rs13319878, rs6437715, rs2162185, rs1515542, rs2270785, rs9830294, rs1439024, rs6762443, rs888507, rs6794467, rs12490248, rs1477886, rs4833103, rs3796547, rs17779822, rs2366711, rs16849146, rs1894292, rs12640320, rs3805284, rs12500426, rs4699312, rs17021918, rs7679673, rs2047408, rs2647262, rs12506850, rs7658048, rs2078277, rs12505546, rs13113975, rs4246742, rs2736098, rs401681, rs11134144, rs10060513, rs40485, rs2087724, rs1482679, rs16901841, rs1295683, rs2070874, rs7752029, rs2018334, rs9358913, rs1140809, rs409558, rs3096702, rs9267911, rs2025645, rs9359428, rs6569371, rs2813532, rs1933488, rs712242, rs6934898, rs9456490, rs651164, rs3120137, rs9364554, rs9457937, rs10486562, rs10807843, rs7801918, rs6962297, rs2465796, rs6957416, rs7777631, rs2272316, rs6961773, rs2132276, rs13265330, rs16887736, rs2911756, rs2272668, rs2339654, rs1380862, rs9297746, rs12543663, rs10086908, rs16901922, rs1016343, rs17832285, rs16901979, rs4871779, rs10107982, rs16902094, rs620861, rs17467139, rs6983267, rs9297756, rs10094059, rs7818556, rs1992833, rs986472, rs12552397, rs4273907, rs4237185, rs753032, rs11253002, rs2386841, rs10795841, rs10508422, rs7075945, rs10508678, rs539357, rs10826398, rs3818714, rs7090755, rs10993994, rs4382847, rs1891158, rs10887926, rs10788160, rs6579002, rs10832514, rs7358335, rs1944047, rs3019779, rs10896437, rs12793759, rs7106762, rs7102758, rs2449600, rs585197, rs2509867, rs11568818, rs7125415, rs11601037, rs11222496, rs4570588, rs6489721, rs3213764, rs17395631, rs4423250, rs11168936, rs10875943, rs3759129, rs902774, rs1827611, rs4760442, rs11610799, rs6539333, rs11067228, rs7485441, rs6489794, rs4119478, rs17070292, rs2293710, rs17256058, rs1950198, rs2331780, rs7141529, rs12880777, rs17123359, rs785437, rs524908, rs12903579, rs7178085, rs7164364, rs896615, rs11634741, rs9972541, rs12594014, rs11631109, rs1558902, rs8044335, rs2738571, rs885479, rs385894, rs684232, rs4925094, rs17138478, rs11649743, rs2107131, rs7213769, rs12946864, rs306801, rs138213197, rs1863610, rs17224342, rs9911515, rs12947919, rs966304, rs17744022, rs7234917, rs1943821, rs2227270, rs1363120, rs888663, rs1227732, rs1054564, rs4806120, rs11672691, rs758643, rs3745233, rs6509345, rs2659051, rs2735839, rs1354774, rs2691274, rs6090461, rs2297434, rs6062509, rs2315654, rs2823118, rs2838053, rs398146, rs16988279, rs2269640, rs4822763, rs132774, rs747745, rs5978944, rs6530238, rs5934705, rs5935063, rs4830488, rs17318620, rs5945619, rs5945637, rs11091768, rs2473057, rs5918762, rs4844228, rs6625760 and rs17324573. Even though the use of the complete list is preferable, any subset of this list is suitable for use in the assessment of the presence or non-presence of aggressive prostate cancer in a subject. A subset of a list of SNPs mentioned herein may comprise about 95%, or 90%, or 85%, or 80%, or 75%, or 70%, of the SNPs in the list. The list may also contain other additional SNPs mentioned herein. The SNP in this list (all, or a subset comprising about 95%, or 90%, or 85%, or 80%, or 75%, or 70%, of the SNP in this list) may be placed on the same solid support, for example the same glass slide, for simultaneous detection in a suitable analytical instrument.

Another more preferred collection of SNPs related to PCa further include, but are not limited to rs138213197, rs7818556, rs6983267, rs10993994, rs12793759, rs16901979, rs9911515, rs1016343, rs7106762, rs6579002, rs16860513, rs5945619, rs16902094, rs10896437, rs651164, rs7679673, rs13265330, rs2047408, rs10107982, rs620861, rs9297746, rs1992833, rs7213769, rs2710647, rs888507, rs17021918, rs12500426, rs2028900, rs7102758, rs16901922, rs6062509, rs2659051, rs17832285, rs12543663, rs4699312, rs11091768, rs3120137, rs6794467, rs10086908, rs7141529, rs2315654, rs12151618, rs747745, rs1009, rs2132276, rs2735839, rs11568818, rs684232, rs9364554, rs9830294, rs2660753, rs10807843, rs1933488, rs17467139, rs12947919, rs721048, rs385894, rs2331780, rs1894292, rs2107131, rs6545962, rs11649743, rs758643, rs2297434, rs902774, rs2647262, rs17224342, rs5918762, rs11672691, rs17138478, rs3019779, rs1873555, rs9457937, rs2838053, rs12946864, rs12475433, rs3765065, rs2018334, rs3771570, rs4871779, rs10875943, rs11601037, rs6489721, rs11168936, rs9297756, rs11900952, rs6569371, rs7752029, rs5934705, rs3745233, rs1482679, rs749264, rs6625760, rs5978944, rs2366711, rs5935063, rs10199796, rs2473057, rs4925094, and rs3096702, or a subset thereof. Preferably, when this collection of SNPs is used in a method as defined herein in the context of PCa, this list is combined with one or more of the biomarkers selected from the group consisting of: PSA, free PSA, intact PSA, hK2, MIC-1 and MSMB, such as 1, 2, 3, 4, 5, or 6, from this group, such as at least least three biomarkers of which two is PSA and free PSA. Even though the use of the complete list of SNPs is preferable, any subset of this list is suitable for use in the assessment of the presence or non-presence of aggressive prostate cancer in a subject. The list may also contain other additional SNPs mentioned herein.

A subset of a list of SNPs mentioned herein may comprise about 95%, or 90%, or 85%, or 80%, or 75%, or 70%, of the SNPs in the list.

Further SNPs which are optionally included are selected from the group consisting of rs12490248, rs4245739, rs10094059, rs306801, rs2823118, rs2025645, rs9359428, rs10178804, rs6090461, rs2270785, rs16901841, rs2465796, rs17256058, rs16849146, rs2269640, rs8044335, rs6530238, rs712242, rs9267911, rs11134144, rs12880777, rs7090755, rs132774, rs17779822, rs398146, rs4844228, rs4237185, rs7125415, rs1439024, rs6770955, rs11253002, rs4822763, rs2162185, rs12640320, rs5945637, rs3818714, rs6762443, rs10508678, rs2272668, rs2227270, rs6437715, rs3759129, rs1891158, rs7358335, rs12988652, rs3796547 rs7234917, rs6509345, rs966304, rs1515542, rs11631109, rs871688, s4382847, rs9972541, rs13113975, rs4119478, rs1380862, rs7529518, rs785437, rs1140809, rs4830488, rs10458360, rs2738571, rs11634741, rs1950198, rs539357, rs16887736, rs7658048, rs11222496, rs2207790, rs12506850, rs4512641, rs2813532, rs6934898, rs582598, rs10191478, rs10486562, rs17395631, rs7525167, rs12637074, rs10887926, rs7485441, rs1944047, rs7178085, rs17318620, rs10489871, rs2691274, rs6962297, rs1827611, rs4806120, rs7164364, rs2293710, rs13017302, rs4570588, rs2386841, rs40485, rs524908, rs10795841, rs4273907, rs12612891, rs10496470, rs6755901, rs1943821. rs13319878, rs6957416, rs12552397, rs6489794, rs4346531, rs7777631, rs1046011, rs16988279, rs986472, rs10508422, rs9456490, rs1295683, rs2449600, rs7075945, rs9358913, rs1477886, rs753032, rs409558, rs4246742, rs10060513, rs17070292, rs10826398, rs17744022, rs7801918, rs885479, rs1863610, rs3805284, rs10832514, rs2509867, rs2070874, rs2339654, rs12903579, rs11610799, rs2272316, rs6961773, rs2078277, rs17324573, rs6760417, rs2911756, rs12233245, rs896615, rs4760442, rs2087724, rs439378, rs4833103, rs6539333, rs4423250, rs12594014, rs17123359, rs12505546, and rs585197, or a subset thereof.

The combination of data can be any kind of algorithmic combination of results, such as a linear combination of data wherein the linear combination improves the diagnostic performance (for example as measured using ROC-AUC). Other possible methods for combining into a model capable of producing a diagnostic estimate include (but are not limited to) non-linear polynomials, support vector machines, neural network classifiers, discriminant analysis, random forest, gradient boosting, partial least squares, ridge regression, lasso, elastic nets, k-nearest neighbors. Furthermore, the book "The Elements of Statistical Learning: Data Mining, Inference, and Prediction, Second Edition" by T Hastie, R Tibshirani and J Friedman as published by Springer Series in Statistics, ISBN 978-0387848570 (which is incorporated by reference herein) describes many suitable methods for combining data in order to predict or classify a particular outcome.

The algorithm which turns the data from the different categories into a single value being indicative of if the patient is likely to suffer from solid tumor cancer is preferably a non-linear function, wherein the dependency of different categories is employed for further increasing the diagnostic performance of the method. The algorithm used for predicting the risk for solid tumor cancer may further benefit from using transformed variables, for example by using the log 10(PSA) value for PCa. Transformation is particularly beneficial for variables with a distribution that is deviating clearly from the normal distribution. Possible variable transformations include, but are not limited to, logarithm, inverse, square, and square root. It is further common to center each variable to zero average and unit variance.

In the case of PCa, there are many rational reasons for distinguishing between prostate cancer in general and aggressive prostate cancer. In most cases, prostate cancer is a slowly progressing disease. The fact that most men are diagnosed late in life means that a large fraction of the men diagnosed with prostate cancer die of other causes. Thus, the ability to estimate if an individual is at elevated risk for having aggressive prostate cancer, prior to biopsy, makes it possible for example to motivate the individual to change life-style. To stop smoking, to reach a BMI value below 30 and to exercise regularly (approximately 30 minutes 3-6 days of the week) are all factors that in general promotes survival in conditions of severe disease, including prostate cancer. Another important aspect is dietary issues. Through changing the diet, the PCa development may be reduced. There is evidence suggesting that reduced dietary intake can reduce the risk for onset of PCa as reported by Song and co-authors in the publication "Whole milk intake is associated with prostate cancer-specific mortality among U.S. male physicians." as published in J Nutr. 2013 February; 143(2):189-96 (which is incorporated by reference herein). Similar evidence exists for the positive effects of intake of green tea and intake of soy products. Hence, if an individual is found having elevated risk for aPCa it is reason to suggest to said individual to decrease intake of dairy products and increase intake of green tea and soy based products. For other types of solid tumor cancer, similar recommendations are equally suitable.

The principle of measuring the same biomarker at more than one occasion within a time-frame that is short in comparison to the biology of the solid tumor cancer disease can be embedded in a clinical road-map, wherein there is a predetermined sequence of events in the process of determining if an individual has the solid tumor cancer disease. In the case of PCa, an exemplary workflow could be the following. The initial test could be a blood sample in which the PSA value is determined. This initial test is typically carried out at a doctor's appointment. If the PSA value is higher than an upper threshold, the individual is at high risk of having PCa. If the PSA value is higher than a lower threshold but lower than the upper threshold, the same blood sample is also analyzed for a selected number of other relevant protein biomarkers and a selected number of SNPs to provide further information about the risk for PCa in the individual. In cases where the result of the initial test (irrespective of whether only the PSA value was used or the combination of the PSA value and the additional protein biomarkers and SNP) indicates that the risk for PCa is very high, the individual can be immediately remitted to a specialist. In cases where the result of the initial test indicates that the risk for PCa is high, the individual can be invited to a further doctor's appointment (a follow-up doctor's appointment) within 3-9 weeks. During such a further doctor's appointment, a multitude of tests may be conducted in order to further improve the ability to determine if the individual has PCa, including (but not limited to) a second blood sample so as to provide a basis for the determination of the biomarker kinetics for the biomarkers measured during the first occasion as well as the provision of values for additional biomarkers and additional SNPs, digital rectal examination (DRE) and/or examination to estimate prostate volume, such as by ultrasound examination. In some cases it may be possible to adjust the values for one measured entity through use of a second measured entity. For example, it is known that PSA is produced in prostate tissue, and a large prostate hence produces more PSA than a small prostate. Through the use of a prostate volume estimate, the PSA value can therefore be adjusted for individuals with unusually large or small prostate. This would further be useful for distinguishing benign prostate hyperplasia from PCa. All in all, given the additional information from one or more further doctor's appointments, it would be possible to determine with higher confidence, if the individual is at risk of having PCa. Other suitable actions could also be assigned, such as scheduling another doctor's appointment in the far future for low-risk patients, in the near future for higher risk patients, immediately remitting the individual to a prostate biopsy procedure, or even immediately remitting to therapy.

To put the short term kinetic composite value into a practical context, it can be described as a part of a program for monitoring the risk level for solid tumor cancer disease. Such a program can be developed for any solid tumor cancer, but will be described in a non-limiting manner as a prostate cancer monitoring program. Most solid tumor cancer diseases, including prostate cancer, are relatively uncommon at young age. Hence, individuals are typically invited to participate in the monitoring program when having reached an age where the disease is becoming more common. For prostate cancer, a suitable age to join a monitoring program is between 45 years and 55 years of age. The most likely starting point is for the individual to provide a biological sample, possibly a blood sample, in which protein biomarkers and/or genetic biomarkers indicative of risk for the disease are quantified. For prostate cancer, determination of PSA concentration is highly suitable. It may further be beneficial to determine the concentration of other biomarkers related to prostate cancer, such as kallikrein-like biomarkers, MSMB, GSTP1, AMACR, and MIC-1. It may also be suitable to determine genetic properties of the individual, such as determining if the individual is carrier of the HOXB13 SNP (rs138213197) which alone indicates that the individual has 3-4 times higher risk than the average individual to get prostate cancer. It may further be suitable to combine measurements with patient information, such as age, family history, and co-morbidities (to mention a few non-limiting examples). The results from the initial protein and gene biomarker tests are combined into an individual risk estimate for having the disease. Based on the risk estimate, the individual can be categorized and handled in different manners. If the risk estimate indicates much lower than average risk, it can for example be recommended that another test is taken after 2-5 typical tumor volume doubling times. For prostate cancer, the typical tumor doubling time is approximately 2 years, so in this case a re-test recommendation in 4-10 years could be appropriate. If the risk estimate indicates average risk, it can for example be recommended that another test is taken after 1-2 typical tumor volume doubling times, which for prostate cancer would be 2-4 years. If the risk estimate indicates elevated risk, it can for example be recommended that the individual is referred to a doctor for initial evaluation. Finally, there will likely be cases where the risk estimate is so high that that individual can be directly referred to advanced diagnostic procedures (biopsy, PET-scan, and the similar) or even therapy. In the case of prostate cancer, the PSA value alone sometimes serves as the biomarker used for determining which category an individual belongs to, where the low risk group has PSA less than 1 ng/mL, the average risk group has PSA value in the range of 1 to 3 or 4 ng/mL, the elevated risk group has PSA value in the range of 3 or 4 to approximately 10 ng/mL and the acute risk is PSA value greater than approximately 10 ng/L. The PSA value alone has moderate diagnostic performance, and recent disclosures have shown that diagnostic performance can be improved by combining the PSA value with values of other protein biomarkers and genetic biomarkers, for example as disclosed in WO2013172779 and WO2014079865.

For the individuals that have elevated but not acute risk for having the disease, typically a doctor's appointment would be recommended within approximately 10% of the doubling time, i.e. within approximately 2-3 month for prostate cancer. During such an appointment, the individual will likely be examined and additional tests may be taken. During such an appointment, it is also possible to take a second test of the protein biomarkers used for the initial risk evaluation, so as to create the data necessary for a kinetic composite value. In the case of prostate cancer, a re-test of PSA and other kallikrein-like biomarkers would be beneficial for improving the risk estimate through short term PSA kinetic composite value. The output of the doctor's appointment and the complementing tests is a more precise risk evaluation, and may result in the individual being recommended to proceed to additional diagnostic procedures (such as a biopsy procedure), or to proceed directly to therapy, or to categorizing the individual to a lower risk level where a re-test is justified in 1-2 or even 2-10 typical doubling times of the solid tumor cancer.

When an individual joins such a structured monitoring program, the chances that a solid tumor cancer is detected early is increased which in turn (in average) leads to milder treatment, less sick leave days and improved survival statistics for the individuals that are in fact developing the solid tumor disease.

Accordingly, there is in another aspect related to herein a method for indicating a presence or a non-presence of a PCa in an individual comprising:

A. measuring a presence or concentration of at least one PCa related biomarker, such as (total) PSA, in a first biological sample from an individual originating from a first point in time, B. in case multiple biomarkers are measured, combining data regarding the presence or concentration of the biomarker values into a composite value or a biomarker value, and thereafter
  i) if the biomarker value (for single biomarker measurement) or the composite value (for multiple biomarkers) in said first biological sample, is lower than or equal to a predetermined low-risk level which is reflecting low risk for prostate cancer, recommend to make another test in 3-10 years (Green light), or
  ii) if the biomarker value (for single biomarker measurement) or the composite value (for multiple biomarkers) in said first biological sample, is higher than or equal to a predetermined high-risk level which is reflecting high risk for prostate cancer, recommend to refer said individual to a confirmatory diagnostic procedure, such as a biopsy (Red Light), or
  iii) if the biomarker value (for single biomarker measurement) or the composite value (for multiple biomarkers) in said first biological sample, is between the low-risk level and the high-risk level, subjecting said biological sample to additional follow-up evaluation or testing to determine if:
    a) said individual has high risk and should be referred to a confirmatory diagnostic procedure, such as a biopsy (Red Light), or
    b) if said individual has intermediate risk for prostate cancer, recommend to make another test in 1-3 years (Yellow light), wherein an additional follow-up evaluation conducted with a biological sample originating from a first point in time comprises measuring in said biological sample the presence or concentration of one or more of, the biomarkers selected from the group consisting of: PSA, free PSA, intact PSA, hK2, MIC-1 and MSMB and/or determining the presence or absence of one or more of genetic SNP markers selected from the group consisting of: rs138213197, rs7818556, rs6983267, rs10993994, rs12793759, rs16901979, rs9911515, rs1016343, rs7106762, rs6579002, rs16860513, rs5945619, rs16902094, rs10896437, rs651164, rs7679673, rs13265330, rs2047408, rs10107982, rs620861, rs9297746, rs1992833, rs7213769, rs2710647, rs888507, rs17021918, rs12500426, rs2028900, rs7102758, rs16901922, rs6062509, rs2659051, rs17832285, rs12543663, rs4699312, rs11091768, rs3120137, rs6794467, rs10086908, rs7141529, rs2315654, rs12151618, rs747745, rs1009, rs2132276, rs2735839, rs11568818, rs684232, rs9364554, rs9830294, rs2660753, rs10807843, rs1933488, rs17467139, rs12947919, rs721048, rs385894, rs2331780, rs1894292, rs2107131, rs6545962, rs11649743, rs758643, rs2297434, rs902774, rs2647262, rs17224342, rs5918762, rs11672691, rs17138478, rs3019779, rs1873555, rs9457937, rs2838053, rs12946864, rs12475433, rs3765065, rs2018334, rs3771570, rs4871779, rs10875943, rs11601037, rs6489721, rs11168936, rs9297756, rs11900952, rs6569371, rs7752029, rs5934705, rs3745233, rs1482679, rs749264, rs6625760, rs5978944, rs2366711, rs5935063, rs10199796, rs2473057, rs4925094, and rs3096702, or a subset thereof, so as to attempt to determine if said individual has intermediate risk (Yellow Light) or high risk (Red Light) by combining all the obtained results related to the individual, wherein an additional follow-up evaluation is optionally conducted at a second point in time if necessary to determine risk level, said evaluation comprises one or more of: a digital rectal examination (DRE) (doctors appointment), a prostate volume determination (doctors appointment), collecting patient history; and/or measuring a biomarker presence or concentration of a biological sample originating from said second point in time, and thereafter combine all the obtained results related to the individual, such as combining data based on: the presence or concentration of the at least one biomarker in the first biological sample originating from a first point in time and/or on one or more of the result(s) of the follow-up evaluation to form a composite value and compare it with a pre-determined cut-off value established with control samples of known predefined solid prostate cancer and benign disease diagnosis reflecting high-risk or intermediate-risk for prostate cancer (Red light or Yellow light), wherein said the at least one biomarker determined is the same biomarker in each of the biological samples.

Said additional follow-up evaluation may further also comprise determining the presence or absence of one or more of genetic SNP markers selected from the group consisting of rs12490248, rs4245739, rs10094059, rs306801, rs2823118, rs2025645, rs9359428, rs10178804, rs6090461, rs2270785, rs16901841, rs2465796, rs17256058, rs16849146, rs2269640, rs8044335, rs6530238, rs712242, rs9267911, rs11134144, rs12880777, rs7090755, rs132774, rs17779822, rs398146, rs4844228, rs4237185, rs7125415, rs1439024, rs6770955, rs11253002, rs4822763, rs2162185, rs12640320, rs5945637, rs3818714, rs6762443, rs10508678, rs2272668, rs2227270, rs6437715, rs3759129, rs1891158, rs7358335, rs12988652, rs3796547 rs7234917, rs6509345, rs966304, rs1515542, rs11631109, rs871688, s4382847, rs9972541, rs13113975, rs4119478, rs1380862, rs7529518, rs785437, rs1140809, rs4830488, rs10458360, rs2738571, rs11634741, rs1950198, rs539357, rs16887736, rs7658048, rs11222496, rs2207790, rs12506850, rs4512641, rs2813532, rs6934898, rs582598, rs10191478, rs10486562, rs17395631, rs7525167, rs12637074, rs10887926, rs7485441, rs1944047, rs7178085, rs17318620, rs10489871, rs2691274, rs6962297, rs1827611, rs4806120, rs7164364, rs2293710, rs13017302, rs4570588, rs2386841, rs40485, rs524908, rs10795841, rs4273907, rs12612891, rs10496470, rs6755901, rs1943821. rs13319878, rs6957416, rs12552397, rs6489794, rs4346531, rs7777631, rs1046011, rs16988279, rs986472, rs10508422, rs9456490, rs1295683, rs2449600, rs7075945, rs9358913, rs1477886, rs753032, rs409558, rs4246742, rs10060513, rs17070292, rs10826398, rs17744022, rs7801918, rs885479, rs1863610, rs3805284, rs10832514, rs2509867, rs2070874, rs2339654, rs12903579, rs11610799, rs2272316, rs6961773, rs2078277, rs17324573, rs6760417, rs2911756, rs12233245, rs896615, rs4760442, rs2087724, rs439378, rs4833103, rs6539333, rs4423250, rs12594014, rs17123359, rs12505546, and rs585197, or a subset thereof.

The data regarding the presence or concentration of the at least one biomarker in a biological sample originating from said second point in time is useful for creating the data necessary for forming a kinetic composite value as next step.

A subset of a list of SNPs may comprise about 95%, or 90%, or 85%, or 80%, or 75%, or 70%, of the SNPs in a list. The list may also contain other additional SNPs mentioned herein. The SNP in this list (all, or a subset comprising about 95%, or 90%, or 85%, or 80%, or 75%, or 70%, of the SNP in this list) may be placed on the same solid support, for example the same glass slide, for simultaneous detection in a suitable analytical instrument.

In one aspect, the additional follow-up evaluation conducted at a second point in time further comprises a risk evaluation comprising combining data regarding the presence or concentration of the at least one biomarker in said samples originating from a first and a second point in time, wherein said at least one biomarker determined is the same biomarker in each of the biological samples and wherein the time period between the origin of the first and the second biological sample is about three months, to form a kinetic composite value that reflects the change of biomarker presence or concentration in said biological samples between the first and the second point in time. How such a kinetic composite value is calculated is previously described herein. Other time periods mentioned herein in relation to PCa are also applicable to the method.

The invention is now further exemplified in the following experimental section. The examples provided therein are merely illustrating and not limiting for the present invention.

Example 1

To illustrate the current invention, a data set comprising 436 individuals who were subjected to prostate cancer screening within the STHLM3 clinical trial was studied. The selected individuals matched the following criteria:
a. The initial PSA test resulted in a value of total PSA below 10 ng/mL.
b. The individual was selected for biopsy.
c. At the time of biopsy, a second blood test was taken and a second PSA test was taken and the corresponding PSA value was determined.
d. The change in PSA value was less than 100%.

The individuals were admitted to biopsy and second PSA test typically within 10-30 days, but in some cases the time between the initial PSA test and the second PSA test was two or three months. In this cohort, 175 individuals had less than 10% change of the PSA values. 129 individuals had PSA values that decreased between 10% and 73% of the initial PSA value and 101 had PSA values that increased between 10% and 100% of the initial PSA value. Based on this data set, it was observed that individuals with a small difference between the initial and the second PSA test were overrepresented in terms of prostate cancer diagnosis. Of the 116 individuals having a small variability of the PSA value, 18% had aPCa. For the individuals with decreasing PSA values 12% had aPCa and for individuals with increasing PSA values 12% had aPCa.

In order to illustrate how this finding could be applied in a prostate cancer screening setting, two different models were applied for predicting the risk for an individual receiving a biopsy with rank Gleason Score 7 or higher. Gleason score 7 or greater is indicative of advanced prostate cancer. The first model was based on the initial PSA value alone, i.e.

$$Y1 = PSA1value$$

The Y1 model was assessed for its ability to predict aggressive prostate cancer using a ROC graph in which ROC-AUC was determined to 0.57 when using the first PSA value. In a second model, the initial PSA value was combined with the PSA kinetics, i.e. the change in PSA value based on the repeated PSA test, to form a kinetic composite value, Y2, which reflects the change in PSA concentration.

$$Y2 = 1 + 0.7*PSA1value - 10.9*ABS((PSA2value - PSA1value)/PSA1value)$$

wherein PSA1value is the result from the first PSA test, PSA2value is the result from the second PSA test and ABS(x) denotes the absolute value of the argument x. The Y2 model was assessed for its ability to predict aggressive prostate cancer and ROC-AUC was determined to 0.64.

The ROC curves for the two models are depicted in FIG. 1, wherein the solid curve 100 shows the Y2 model and the dashed curve 110 shows the Y1 model.

Hence, the individuals with a robust level of PSA (less than approximately 10% change) had a higher incidence of Gleason 7 prostate cancer (i.e. aggressive prostate cancer) than the individuals having a varying PSA value. A decreasing PSA value between the two tests is indicative of lower risk for aggressive prostate cancer. Surprisingly, also an increasing PSA value in the time frame of 2-12 weeks is indicative of lower risk for aggressive prostate cancer as compared to robust PSA value. Thus, through a second PSA test taken within 3 months from the initial PSA test, it is possible to better estimate if a biopsy should be excised.

Example 2

In order to illustrate that the invention is of a more general nature, a data set comprising 326 individuals who were subjected to prostate cancer screening within the STHLM3 clinical trial was studied. The selected individuals matched the following criteria:
a. The initial PSA test resulted in a value of total PSA below 10 ng/mL. At the same time, MIC-1 and MSMB values were determined.
b. The individual was selected for biopsy.
c. At the time of biopsy, a second blood test was taken and a second blood test was taken and the corresponding values of PSA, MIC-1 and MSMB were determined.
d. The change in the biomarker value under study was less than 100%.

The individuals were admitted to biopsy and a second PSA test typically within one month, but in some cases the time between the initial PSA test and the second PSA test was two or three months. Approximately 13% of the individuals in this cohort proved to have aPCa. As shown in Table 1, the three biomarkers in this cohort had clear differences in terms of variation pattern depending on cancer status. For the biomarker MIC-1, of the 213 individuals that did not have prostate cancer, 43% had a stable MIC-1 value (defined as changing less than 10%) when the results from the two different test occasions were compared. 37% of these individuals had a clearly decreasing value (i.e. the MIC-1 biomarker concentration had decreased more than 10% when the second test result was compared to the first). The remaining 20% of these individuals had more than 10% increased concentration of MIC-1 when the second test result was compared to the first. For the 44 individuals with confirmed aggressive prostate cancer, 50% had a stable MIC-1 concentration when the second test result was compared to the first, which is a larger fraction than within the group of individuals who did not have prostate cancer. This indicates that a stable MIC-1 value is to some extent correlated with an increased risk of having aPCa. For the biomarker MSMB, 17% of the individuals who did not have cancer had stable MSMB values, while 31% of the individuals with aPCa had stable MSMB values. This indicates that a stable MSMB value is correlated with an increased risk of having aPCa. The same is valid for the total PSA value, for which 38% of the individuals without cancer had a stable value, as compared to 60% of the individuals with aPCa. All in all, this example shows that the finding that a stable protein biomarker value over a 1-3 month period is correlated to increased risk of having aggressive prostate cancer is not limited to PSA, but is valid also for other protein biomarkers, including MSMB and MIC-1.

TABLE 1

|  | MIC-1 | MSMB | total PSA |
|---|---|---|---|
| No cancer | N = 213 | N = 193 | N = 197 |
| DECREASE more than 10% | 37% | 23% | 34% |
| STABLE | 43% | 17% | 38% |
| INCREASE more than 10% | 20% | 60% | 29% |
| Gleason score = 7 or 8 or 9 | N = 44 | N = 39 | N = 40 |
| DECREASE more than 10% | 32% | 18% | 20% |
| STABLE | 50% | 31% | 60% |
| INCREASE more than 10% | 18% | 51% | 20% |

Example 3

After collecting patient samples during a longer time, the data set of example 1 had been extended to comprise 1616 individuals who were subjected to prostate cancer screening within the STHLM3 clinical trial. Values for these was studied. The selected individuals matched the following criteria:
a. The initial PSA test resulted in a value of total PSA below 10 ng/mL.
b. The individual was selected for biopsy.
c. At the time of biopsy, a second blood test was taken and a second PSA test was taken and the corresponding PSA value was determined.
d. The change in PSA value was less than 100%

Figure 2:
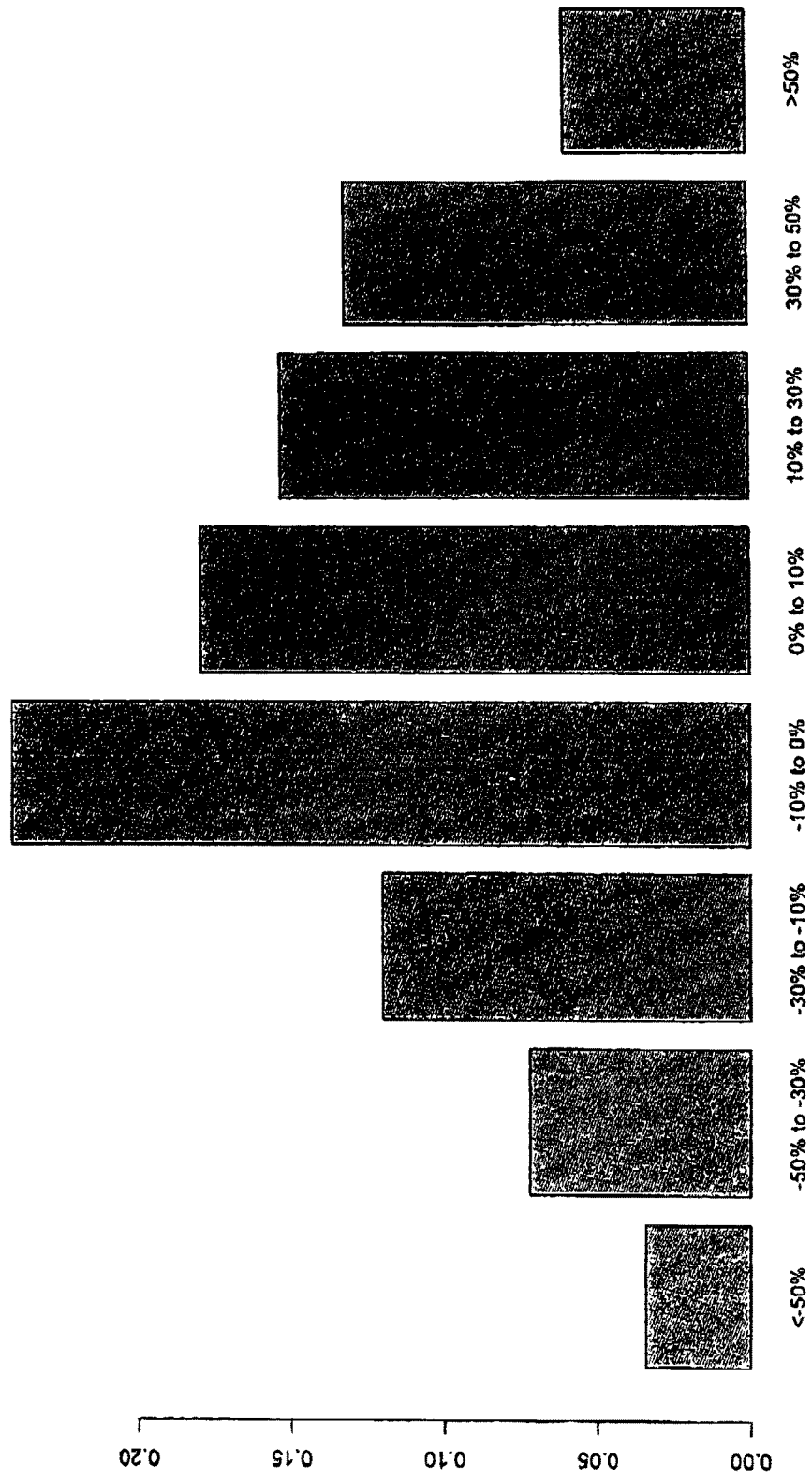
FIG. 2 shows a bar graph indicating the risk for an individual having aggressive prostate cancer (aPCa) as a function of the change of PSA value.

The individuals were admitted to biopsy and second PSA test typically within 10-30 days, but in some cases the time between the initial PSA test and the second PSA test was two or three months. FIG. 2 shows the risk for aPCa (y-axis), in this case defined as Gleason score=7, 8, 9, or 10, as a function of the extent of change in PSA value. Individuals who had almost the same PSA value, i.e. value changing less than 10% up or 10% down, the risk for having aPCa was greater than 16% (i.e. 0.16 on the y-axis scale). For individuals where the PSA value decreased more than 10% during the short time between the two blood samples, the risk of having aPCa was clearly lower than 16%, actually approaching 3% for the individuals with largest decrease. For individuals who had an increase of PSA values greater than 10%, the risk was lower than for the individuals who had no or little change of PSA value. The risk reduction related to PSA value increase was clear and significant, but not as strong as for PSA decrease. When evaluating which time intervals gave the best performance in terms of ability of predicting aPCa, it was noted that the best time interval was 14-42 days. For individuals who had 14-42 days separation between the blood samples, the odds ratio for PSA increase greater than 10% was 0.63-0.66, and for decrease greater than 10% the odds ratio was 0.29-0.44. For shorter time intervals, both increase and decrease exceeding 10% of PSA value are related to lower risk of aPCa, but here increase of PSA value greater than 10% was a stronger indication of reduced risk (Odds ratio=0.29) as compared to PSA decrease greater than 10% (Odds ratio 0.54). For longer time intervals between blood samples, the ability to predict presence of aPCa gradually decreases. At 49 days separation between the two samples, a clear change in PSA value (exceeding 10%) was weakly related to lower risk for aPCa, and at 56 days separation the change in PSA value did not have any ability to predict aPCa given the definition of change as more than 10% increase or decrease.

Example 4

Figure 3:
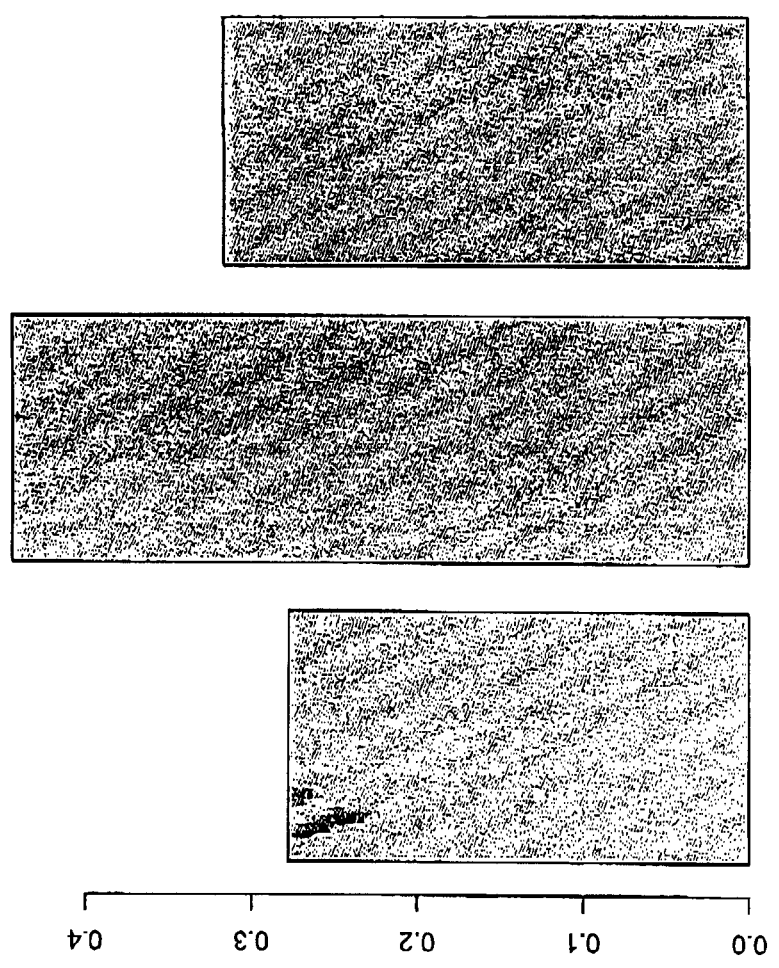
FIG. 3 shows a bar graph indicating the risk for an individual having PCa as a function of the change of PSA value.

The data set of example 3 was evaluated for the ability to predict overall prostate cancer. FIG. 3 shows the risk for PCa (y-axis), in this case defined as Gleason score=6, 7, 8, 9, or 10, as a function of the extent of change in PSA value. The risk for an individual who has stable PSA value (defined as variation less than 10% up or down) to have PCa is greater than 40%. The risk for an individual who has varying PSA Value, either more than 10% increase or 10% decrease, is approximately 30%. This means that variability of the PSA value is indicative of reduced risk for overall prostate cancer as well Example 5

Figure 4:
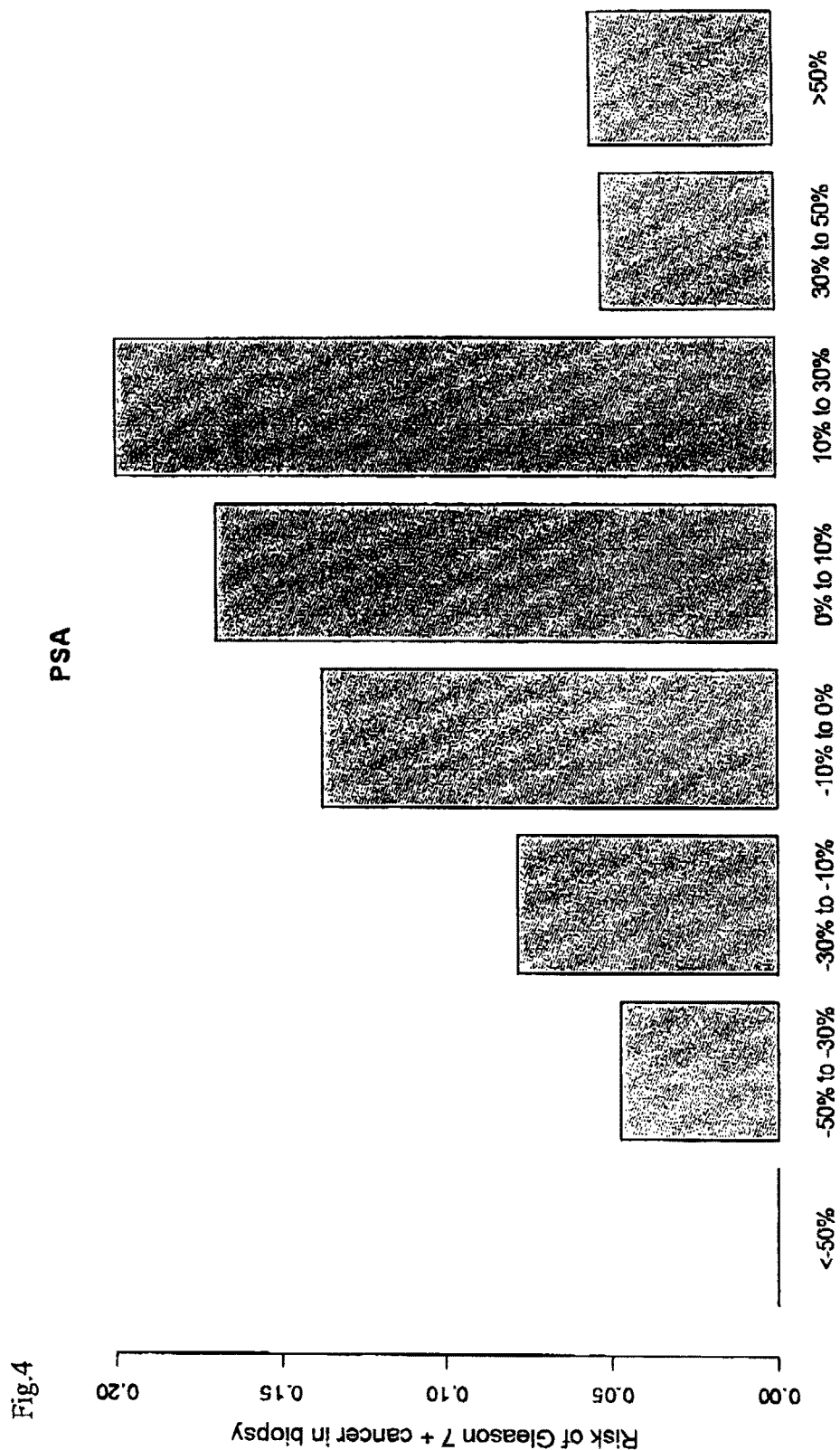
FIG. 4 shows a bar graph indicating the risk for an individual having aggressive prostate cancer (aPCa) as a function of the change of PSA value, focused on individuals with 35 days to 63 days between the two samples.

The data set of example 3 was evaluated using a different definition of change. Firstly, the definition of change of PSA value was selected to be change greater than 30% (i.e. more than 30% increase or more than 30% decrease). Secondly, individuals who had 35-63 days between the first and the second sample were evaluated. FIG. 4 shows the risk for aPCa (y-axis), in this case defined as Gleason score=7, 8, 9, or 10, as a function of the extent of change in PSA value for individuals who had 35-63 days between the first and the second sample. The risk for an individual who has stable PSA value (defined as variation less than 30% up or down) to have PCa is greater than 7-20%. The risk for an individual who has varying PSA Value, either more than 30% increase or 30% decrease, is approximately 5%. This means that large variability of the PSA value is indicative of reduced risk for aggressive prostate cancer for individuals for which 35-63 days passed between the two samples.

Example 6

The STHLM3 clinical trial evaluates a prostate cancer monitoring program. This example is based on a large proportion of study, where 47610 individuals had joined the trial and had taken a first blood sample. This first blood sample was initially characterized with respect to PSA value and freePSA value. For individuals with PSA value lower than 1 ng/mL, the risk for prostate cancer is low and the recommendation was to make another PSA test in 3-10 years. This was communicated as a Green Light to these individuals. For individuals with a PSA value greater than or equal to 10 ng/mL, the risk for prostate cancer is high and the recommendation was to perform a biopsy. This was communicated as a Red Light to these individuals. For individuals with PSA value between 1 and 10 ng/mL, the blood sample was subjected to additional follow-up testing, comprising the determination of 6 biomarkers (PSA, free PSA, intact PSA, hK2, MIC-1 and MSMB) and 254 genetic SNP markers (rs138213197, rs7818556, rs6983267, rs10993994, rs12793759, rs16901979, rs9911515, rs1016343, rs7106762, rs6579002, rs16860513, rs5945619, rs16902094, rs10896437, rs651164, rs7679673, rs13265330, rs2047408, rs10107982, rs620861, rs9297746, rs1992833, rs7213769, rs2710647, rs888507
rs17021918, rs12500426, rs2028900, rs7102758, rs16901922, rs6062509, rs2659051, rs17832285, rs12543663, rs4699312, rs11091768, rs3120137, rs6794467, rs10086908, rs7141529, rs2315654, rs12151618, rs747745, rs1009, rs2132276, rs2735839, rs11568818, rs684232, rs9364554, rs9830294, rs2660753, rs10807843, rs1933488, rs17467139, rs12947919, rs721048, rs385894, rs2331780, rs1894292, rs2107131, rs6545962, rs11649743, rs758643, rs2297434, rs902774, rs2647262, rs17224342, rs5918762, rs11672691, rs17138478, rs3019779, rs1873555, rs9457937, rs2838053, rs12946864, rs12475433, rs3765065, rs2018334, rs3771570, rs4871779, rs10875943, rs11601037, rs6489721, rs11168936, rs9297756, rs11900952, rs6569371, rs7752029, rs5934705, rs3745233, rs1482679, rs749264, rs6625760, rs5978944, rs2366711, rs5935063, rs10199796, rs2473057, rs4925094, rs3096702, rs12490248, rs4245739, rs10094059, rs306801, rs2823118, rs2025645, rs9359428, rs10178804, rs6090461, rs2270785, rs16901841, rs2465796, rs17256058, rs16849146, rs2269640, rs8044335, rs6530238, rs712242, rs9267911, rs11134144, rs12880777, rs7090755, rs132774, rs17779822, rs398146, rs4844228, rs4237185, rs7125415, rs1439024, rs6770955, rs11253002, rs4822763, rs2162185, rs12640320, rs5945637, rs3818714, rs6762443, rs10508678, rs2272668, rs2227270, rs6437715, rs3759129, rs1891158, rs7358335, rs12988652, rs3796547 rs7234917, rs6509345, rs966304, rs1515542, rs11631109, rs871688, s4382847, rs9972541, rs13113975, rs4119478, rs1380862, rs7529518, rs785437, rs1140809, rs4830488, rs10458360, rs2738571, rs11634741, rs1950198, rs539357, rs16887736, rs7658048, rs11222496, rs2207790, rs12506850, rs4512641, rs2813532, rs6934898, rs582598, rs10191478, rs10486562, rs17395631, rs7525167, rs12637074, rs10887926, rs7485441, rs1944047, rs7178085, rs17318620, rs10489871, rs2691274, rs6962297, rs1827611, rs4806120, rs7164364, rs2293710, rs13017302, rs4570588, rs2386841, rs40485, rs524908, rs10795841, rs4273907, rs12612891, rs10496470, rs6755901, rs1943821. rs13319878, rs6957416, rs12552397, rs6489794, rs4346531, rs7777631, rs1046011, rs16988279, rs986472, rs10508422, rs9456490, rs1295683, rs2449600, rs7075945, rs9358913, rs1477886, rs753032, rs409558, rs4246742, rs10060513, rs17070292, rs10826398, rs17744022, rs7801918, rs885479, rs1863610, rs3805284, rs10832514, rs2509867, rs2070874, rs2339654, rs12903579, rs11610799, rs2272316, rs6961773, rs2078277, rs17324573, rs6760417, rs2911756, rs12233245, rs896615, rs4760442, rs2087724, rs439378, rs4833103, rs6539333, rs4423250, rs12594014, rs17123359, rs12505546, and rs585197). Even though the use of the complete list is preferable, any subset of this list is suitable for use in the assessment of the presence or non-presence of aggressive prostate cancer in a subject. Preferred parts thereof are also mentioned herein. Further, a subset of a list of SNPs may comprise about 95%, or 90%, or 85%, or 80%, or 75%, or 70%, of the SNPs of said list. The SNP in this list (all, or a subset comprising about 95%, or 90%, or 85%, or 80%, or 75%, or 70%, of the SNP in this list) may be placed on the same solid support, for example the same glass slide, for simultaneous detection in a suitable analytical instrument.

Furthermore, at the doctor's appointment, a digital rectal examination (DRE) and a prostate volume determination were conducted. Patient history was collected from the individual though a web-based questionnaire. Based on the results of the additional measurements and examinations, the contribution to a risk score was evaluated:

| Biomarker, cumulatively added | ROC-AUC |
|---|---|
| Total PSA | 0.61 |
| Age | 0.61 |
| Family history | 0.61 |
| Previous biopsies | 0.61 |
| Genetic score | 0.66 |
| MSMB | 0.67 |
| MIC1 | 0.67 |
| Free PSA | 0.70 |
| Intact PSA | 0.72 |
| HK2 | 0.72 |
| Prostate volume | 0.76 |
| DRE | 0.76 |

In STHLM3, 44% of the participants received a Green Light message, i.e. they had PSA value less than 1 ng/mL. About 1% of the individuals had PSA value of 10 ng/mL and above, and hence received a Red Light message and a referral to prostate biopsy procedure. The remaining 55% of the individuals had a PSA value between 1 and 10 ng/mL, and for these individuals the extended biomarker analysis was conducted. Risk for cancer was estimated using the following equation:

$$\ln(p/(1-p))=1.64-0.39*\text{sqrt}(\text{FUmic1})-1.09*\text{sqrt}(\text{FUmsmb})+6.98*\text{FUhk2}-0.075*\text{sqrt}(\text{FUpsa})-2.03*\text{sqrt}(\text{FUfreePsaTF})-2.74*\text{sqrt}(\text{FUpsa/FUfreepsa}))+4.1*\text{FUintactPsa}-0.42*\text{sqrt}(\text{INpsa})+2.51*\text{sqrt}(\text{INfreePsa})-9.4*\text{sqrt}(\text{INfreepsa/INpsa})+0.063*\text{age}+0.50*\text{FUgeneticScore}+0.069*\text{familyHistory}-0.43*\text{previousBiopsy}+0.95*\text{dre}-0.45*\text{sqrt}(\text{volume})$$

where $\ln(p/(1-p))$ is the logarithm of the odds related to aggressive prostate cancer (defined as gleason 7 or higher), where FUmic1, FUmsmb, FUhk2, FUpsa, FUfreepsa, FUintactPSA, and refer to values of MIC-1, MSMB, hK2, PSA, free PSA, and intact PSA (in arbitrary units that are closely related to ng/mL) obtained in the follow-up measurement, where FUgeneticScore refers to genetic score obtained in the follow-up measurement, where INpsa and INfreepsa refer to the PSA and free PSA values obtained in the first measurement of the first blood sample (in units ng/mL), where dre and volume refer to the result of Digital rectal examination (1 or 0) and prostate volume (in mL), where age indicates the age (in years) of the individual, where family history indicates if a father or brother to the individual has had prostate cancer (1 or 0), and where previous biopsy indicates if a previous (negative) biopsy has been conducted on the individual (1 or 0).

The equation for calculating the logarithm of the odds can be slightly modified without compromising overall performance. As seen in the list of ROC-AUC increases when cumulatively adding the different information carriers, no single one is absolutely critical, possibly with the exception of the Total PSA value. This means that if one biomarker (such as intact PSA) or one information carrier (such as age)

is omitted from the data set and a new equation for calculating the logarithm of the odds is created, the overall performance will be almost the same as presented for the full equation in this example. Removing multiple biomarkers and/or information carriers, in particular more than 3 biomarkers and/or information carriers, will have visible effect on the performance.

The logarithm of the odds of having prostate cancer was combined with the PSA value to determine if the individual had moderate risk for prostate cancer leading to a recommendation to make another PSA test in 1-3 years, communicated as a Yellow Light. If the individual had elevated risk for prostate cancer, the recommendation was to perform a biopsy, which was communicated as a Red Light. The values used to discriminate Yellow light from Red light reported in this example relies on the cutoff values (PSA value >3 ng/mL or (logarithm of the odds) >−2.2). The resulting sensitivity is ~0.85 and the specificity is ~0.45. In clinical practice, the selected cutoff values used for referring individuals to biopsy depends on a multitude of regional factors. One non-limiting possibility would for example be to use PSA value >4 ng/mL or (logarithm of the odds) >−1.3, which would have a lower sensitivity (~0.6) but higher specificity (~0.76) than the cutoff values used in this example.

Of the approximately 26000 individuals who were in the PSA 1-10 ng/mL category, approximately 7000 were recommended to perform a biopsy. Biopsy was conducted 1-12 weeks after the first blood sample, and most commonly 2-7 weeks after first blood sample. When an individual arrived for biopsy, a second blood test was taken and it was subjected to the follow-up biomarker measurement described above. In the trial, all subjects were biopsied irrespective of biomarker results for the second blood sample and approximately 61% of the biopsies were negative, 22% detected prostate cancer of Gleason 6, and 17% detected aggressive prostate cancer of Gleason 7 or higher.

If the above procedure would have been conducted using the PSA value alone as indicator whether a biopsy should be recommended, the number of biopsy recommendation would increase and the number of negative biopsies would increase. Using a PSA value cutoff of 4.0 ng/mL as the current standard procedure for referral to biopsy (which is the current clinical practice in Sweden) the method described in this example would save 37% of the biopsies at the same sensitivity level for aggressive prostate cancer, i.e. 37% fewer biopsies would be required to identify the same number of aggressive cancers as compared to PSA value alone. In this work-flow, the risk estimate for each individual could have been amended at the time of receiving results from the second blood sample (taken at time of biopsy) so as to use PSA short term kinetics to refine the risk estimate. A PSA kinetic composite value (PSAkcv) could be constructed in the following manner:

PSAkcv=1 if (PSAsecond−PSAfirst)/PSAfirst*100>10

PSAkcv=1 if (PSAsecond−PSAfirst)/PSAfirst*100<−10

Otherwise PSAkcv=0

Adding the PSAkcv to the risk assessment has the ability to improve diagnostic performance with approximately 0.01 to 0.03 units of ROC-AUC, and would further reduce the number of biopsies required to save additional percentages of the biopsies at the same sensitivity level for aggressive prostate cancer, as compared to PSA alone. From an ethical perspective, it is important to mention that this invention was conceived during the clinical trial, and that the trial as such could not be changed after having started. Furthermore, only after having access to retrospective data after completion of the trial, it could be confirmed that short term PSA kinetics is indeed a strong indicator of prostate cancer risk.

Although the invention has been described with regard to its preferred embodiment, which constitutes the best mode currently known to the inventor, it should be understood that various changes and modifications as would be obvious to one having ordinary skill in this art may be made without departing from the scope of the invention as set forth in the claims appended hereto.

The invention claimed is:

1. A method for indicating a presence or non-presence of a predefined solid tumor cancer in an individual, comprising:
    A. Providing at least one biological sample originating from said individual at a first point in time;
    B. Providing at least one biological sample originating from said individual at a second point in time;
    C. In said at least two biological samples, measuring a presence or concentration of at least one biomarker related to said predefined solid tumor cancer;
    D. Combining data regarding the presence or concentration of the at least one biomarker to form a kinetic composite value that reflects the change of biomarker presence or concentration;
    E. Correlating the kinetic composite value to the presence or non-presence of said predefined solid tumor cancer in said individual by comparing the kinetic composite value to a pre-determined cut-off value established with control samples of known predefined solid tumor cancer and benign disease diagnosis;
  wherein
    the time period between the first point in time and the second point in time is in the range from 0.1% to 30% of a typical tumor volume doubling time of said predefined solid tumor cancer; and
    the at least one biomarker determined is the same biomarker in each of the biological samples.

2. The method of claim 1, wherein the time period between the first point in time and the second point in time is in the range of about 0.1% to 15% of a typical tumor volume doubling time of said predefined solid tumor cancer.

3. The method of claim 1 wherein the predetermined cut-off value discriminates between (i) a highly variable presence or concentration of the at least one biomarker, which is not related to development of the predefined solid tumor cancer, and (ii) a less variable presence or concentration of the at least one biomarker, which is related to development of the predefined solid tumor cancer.

4. The method of claim 1, wherein the predefined solid tumor cancer is selected from the group consisting of bladder cancer, breast cancer, colorectal cancer, endometrial cancer, kidney cancer, renal cell cancer, lung cancer, pancreatic cancer, prostate cancer, thyroid cancer.

5. The method of claim 1, wherein said solid tumor cancer is prostate cancer (PCa).

6. The method of claim 5, wherein said solid tumor cancer is aggressive prostate cancer (aPCa).

7. The method of claim 5, wherein the time period between the first point in time and the second point in time is from 3 days to 6 months.

8. The method of claim 5, wherein the time period between the first point in time and the second point in time is from about 1 day to 3 months.

9. The method of claim 8, wherein the time period between the first point in time and the second point in time is from about 1 day to 7 weeks and an approximately 10% difference (increase or decrease), or more, between a prostate specific antigen (PSA) concentration or presence in a first and a second biological sample originating from a first and a second point in time is regarded as a change indicating a lower risk for PCa, and an approximately 10% change or less between a prostate specific antigen (PSA) concentration in a first and a second biological sample originating from a first and a second point in time is indicative of a higher risk of developing prostate cancer.

10. The method of claim 6, wherein said at least one biomarker is selected from a group consisting of prostate specific antigen (PSA), free PSA, complexed PSA, pro PSA, intact PSA, total PSA, human prostatic acid phosphatase (PAP), human kallikrein 2 (hK2), early prostate cancer antigen (EPCA), beta-microseminoprotein (MSMB), glutathione S-transferase 7C (GSTP1), α-methylacyl coenzyme A racemase (AMACR), Macrophage Inhibitory Cytokine 1 (MIC-1).

11. The method of claim 10, wherein said at least one biomarker is selected from a group consisting of free PSA, complexed PSA, total PSA, MSMB, MIC-1.

12. The method of claim 10, wherein the at least one biomarker is selected from the group consisting of free PSA, intact PSA, hK2, MIC-1 and MSMB.

13. The method of claim 1, wherein the solid tumor cancer is ovarian cancer and the biomarker is CA125.

14. The method of claim 1, wherein the solid tumor cancer is colorectal cancer and the biomarker is CEA.

15. The method of claim 1, wherein the solid tumor cancer is breast cancer and the biomarker is CA 15-3.

16. The method of claim 1, wherein the solid tumor cancer is pancreatic cancer and the at least one biomarker is selected from a group consisting of CA 19-9 and CEA.

17. The method of claim 1, further comprising
in said at least two biological samples analyzing a category of SNPs related to said predefined solid tumor cancer (SNPst), by measuring a presence or absence of each of a plurality of SNPst;
Combining data regarding said category of SNPst to form a SNPst composite value representing the SNPst-related risk of developing said predefined solid tumor cancer;
Combining the kinetic composite value and the SNPst composite value to form an overall composite value; and
Correlating said overall composite value to the presence or non-presence of said predefined solid tumor cancer in said individual by comparing said overall composite value to a pre-determined cut-off value established with control samples of known predefined solid tumor cancer and benign disease diagnosis.

18. The method of claim 1, wherein the data regarding said at least one biomarker are combined according to a predetermined equation to form said kinetic composite value.

19. The method of claim 17, wherein the data regarding said category of SNPs are combined according to a predetermined equation to form said SNPst composite value.

20. The method of claim 17, wherein said kinetic composite value and said SNPst composite value are combined according to a predetermined equation to form said overall composite value.

21. The method of claim 1, wherein at least steps D and E are conducted by a computer program product in the internal memory of a digital computer.

22. The method of claim 21, wherein the computer product comprises software code for:
in said at least two biological samples, analyzing a category of SNPs related to said predefined solid tumor cancer (SNPst), by measuring a presence or absence of each of a plurality of SNPst;
Combining data regarding said category of SNPst to form a SNPst composite value representing the SNPst-related risk of developing said predefined solid tumor cancer;
Combining the kinetic composite value and the SNPst composite value to form an overall composite value; and
Correlating said overall composite value to the presence or non-presence of said predefined solid tumor cancer in said individual by comparing said overall composite value to a pre-determined cut-off value established with control samples of known predefined solid tumor cancer and benign disease diagnosis.

23. The method of claim 1, wherein the presence or concentration of the at least one biomarker related to said predefined solid tumor cancer is measured with an immunoassay system including a capture reagent adapted to capture the biomarker and a detection reagent adapted to bind to the biomarker and produce a detectable signal.

24. A method for measuring at least one biomarker indicative of a presence or non-presence of a predefined solid tumor cancer in an individual, comprising:
A. Providing at least one biological sample originating from said individual at a first point in time;
B. Providing at least one biological sample originating from said individual at a second point in time;
C. In each of said at least two biological samples, measuring a presence or concentration of the at least one biomarker related to said predefined solid tumor cancer; and
D. Combining data regarding the presence or concentration of the at least one biomarker to form a kinetic composite value that reflects the change of biomarker presence or concentration;
wherein the time period between the first point in time and the second point in time is in the range from 0.1% to 30% of a typical tumor volume doubling time of said predefined solid tumor cancer.

25. The method of claim 24, wherein the time period between the first point in time and the second point in time is in the range of about 0.1% to 15% of a typical tumor volume doubling time of said predefined solid tumor cancer.

26. The method of claim 24, wherein the presence or concentration of the at least one biomarker related to said predefined solid tumor cancer is measured with an immunoassay system including a capture reagent adapted to capture the biomarker and a detection reagent adapted to bind to the biomarker and produce a detectable signal.

* * * * *

UNITED STATES PATENT AND TRADEMARK OFFICE
CERTIFICATE OF CORRECTION

PATENT NO. : 10,451,626 B2
APPLICATION NO. : 15/124769
DATED : October 22, 2019
INVENTOR(S) : Henrik Grönberg Page 1 of 1

It is certified that error appears in the above-identified patent and that said Letters Patent is hereby corrected as shown below:

On the Title Page

Item (30), change "1450274" to --1450274-4--.

Item (30), change "1450420" to --1450420-3--.

Signed and Sealed this
Seventh Day of January, 2020

Andrei Iancu
*Director of the United States Patent and Trademark Office*